United States Patent [19]

Mizuno et al.

[11] Patent Number: 5,294,336

[45] Date of Patent: Mar. 15, 1994

[54] APPARATUS FOR LIQUID CHROMATOGRAPHY FOR SEPARATING AIC COMPONENTS FROM HEMOGLOBIN IN BLOOD

[75] Inventors: Masako Mizuno, Mito; Kenji Tochigi, Hitachi; Yutaka Misawa, Katsuta; Hiroyuki Miyagi, Kokubunji; Yoshio Watanabe, Hitachi; Taro Nogami; Junkichi Miura, both of Katsuta; Yoshinori Takata, Chiba, all of Japan

[73] Assignee: Hitachi, Ltd., Tokyo, Japan

[21] Appl. No.: 896,784

[22] Filed: Jun. 9, 1992

Related U.S. Application Data

[63] Continuation of Ser. No. 578,214, Sep. 6, 1990, abandoned.

[30] Foreign Application Priority Data

Sep. 18, 1989 [JP] Japan .................................. 1-240017

[51] Int. Cl.$^5$ ............................................ B01D 15/08
[52] U.S. Cl. ................................. 210/198.2; 210/85; 210/143; 210/656; 422/70; 436/66; 436/67; 436/161; 530/385; 530/413; 530/416; 530/417
[58] Field of Search .............. 210/85, 143, 198.2, 210/656; 422/70; 436/66, 67, 161; 530/385, 413, 416, 417; 521/28, 30, 38

[56] References Cited

U.S. PATENT DOCUMENTS

| | | | |
|---|---|---|---|
| 3,983,299 | 9/1976 | Regnier | 210/198.2 |
| 4,029,583 | 6/1977 | Chang et al. | 210/198.2 |
| 4,108,603 | 8/1978 | Regnier et al. | 210/656 |
| 4,543,363 | 9/1985 | Yanagihara | 521/38 |
| 4,663,163 | 5/1987 | Hou et al. | 210/198.2 |
| 4,724,207 | 2/1988 | Hou et al. | 210/656 |
| 4,810,391 | 3/1989 | Bruegger | 436/161 |
| 4,840,730 | 6/1990 | Saxena | 210/143 |
| 5,004,546 | 4/1991 | Takahashi et al. | 210/656 |
| 5,019,269 | 5/1991 | Letourneur et al. | 210/198.2 |

FOREIGN PATENT DOCUMENTS

| | | |
|---|---|---|
| 3609021 | 9/1986 | Fed. Rep. of Germany . |
| 59-232102 | 12/1984 | Japan . |
| 60-213863 | 10/1985 | Japan . |
| 63-75558 | 4/1988 | Japan . |

OTHER PUBLICATIONS

A. J. Alpert and F. E. Regnier, J. Chromatography, 185 (1979) 375–377, 382–383.
Z. Deyl, K. Macek, and J. Janak, "Liquid Column Chromatography", vol. 3, Elsevier, Amsterdam, 1975, pp. 339, 348–350.
Clinical Chemistry, 27/7, pp. 1261–1263 (1981).
Diabetes, vol. 29, pp. 623–628 (Aug. 1980).

Primary Examiner—Robert A. Dawson
Assistant Examiner—Sun Uk Kim
Attorney, Agent, or Firm—Antonelli, Terry, Stout & Kraus

[57] ABSTRACT

Stable hemoglobin $A_{lc}$ (s-$A_{lc}$) can be separated from other hemoglobin components and quantitated in a short time by means of a liquid-chromatographic apparatus comprising a separation column packed with a packing material consisting essentially of a porous substance having a carboxyalkyl group combined thereinto, as ion exchanger, a means for injecting a sample into the separation column, a means for passing one or more eluents through the separation column, and a means for detecting hemoglobin, hemoglobin derivatives or glycosylated hemoglobin, the average particle size of the packing material in dry state being 4 μm or less.

10 Claims, 11 Drawing Sheets

APPARATUS FOR LIQUID CHROMATOGRAPHY FOR SEPARATING AIC COMPONENTS FROM HEMOGLOBIN IN BLOOD

This application is a continuation of application Ser. No. 07/578,214, filed Sep. 6, 1990, now abandoned.

BACKGROUND OF THE INVENTION

1. Field of the Invention

The present invention relates to a method for liquid chromatography of a biological or vital component, and an apparatus therefor.

Particularly, it relates to a method for liquid chromatography of glycosylated hemoglobin, and an apparatus therefor.

2. Related Art Statement

Glycosylated hemoglobins are produced by reaction of a sugar in blood to hemoglobin after the sugar enters erythrocytes, depending on the concentration of the sugar. The concentration of stable-$A_{lc}$ (s-$A_{lc}$) among the glycosylated hemoglobins is said to reflect the average sugar concentration for the past 2 to 3 months. The concentration of s-$A_{lc}$ is hardly influenced by physiological factors, as compared with blood sugar level, urinary sugar level and the like, and hence is used for the diagnosis of diabetes and as an indication of the progress toward recovery of a diabetic.

$A_{lc}$ is formed by binding of glucose to the N-terminal of $\beta$-chain of hemoglobins. $A_{lc}$ consists of labile-$A_{lc}$ (l-$A_{lc}$) and stable $A_{lc}$ (s-$A_{lc}$)

Hemoglobin is a conjugated protein having a molecular weight of about 64,000 produced by combination of heme (a pigment) with globin (a protein) and play an important role as an oxygen carrier in the bodies of animals.

When a sugar such as glucose reacts with hemoglobin, release of oxygen becomes difficult, so that supply of oxygen to peripheral blood vessels and tissues becomes difficult. In addition, the structure of the reaction product is fixed, resulting in deformation of blood vessels, etc.

As normal human hemoglobins, those listed in Table 1 are known. The hemoglobin (Hb) of a healthy adult consists of $HbA_0$, $HbA_2$ and HbF, and a product formed by reaction with a sugar and $HbA_0$ is glycosylated hemoglobin ($HbA_1$). GHb ($HbA_1$) consists of $A_{la}$, $A_{lb}$, $A_{lc}$ and the like which are different in the amino acid structure of hemoglobin and the kind of sugar attached to hemoglobin. Of the glycosylated hemoglobins, $A_{lc}$, and by binding of glucose to the N-terminal of $\beta$ chain, is found in the largest amount.

TABLE 1

| | Classification | | Structure | Sugar chain | Content |
|---|---|---|---|---|---|
| Hb | $HbA_0$ | | $\alpha_2\beta_2$ | — | >90% |
| | $HbA_2$ | | $\alpha_2\delta_2$ | — | 2% |
| | HbF | | $\alpha_2\gamma_2$ | — | <1% |
| GHb | $HbA_1$ | $A_{1a1}$ | $\alpha_2(\beta\text{-N-FDP})_2$ | fructose-1,6-diphosphate | <1% |
| | | $A_{1a2}$ | $\alpha_2(\beta\text{-N-G6P})_2$ | glucose-6-phosphate | <1% |
| | | $A_{1b}$ | $\alpha_2(\beta\text{-N-CHO})_2$ | aldehyde | <1% |
| | | $A_{1c}$ | $\alpha_2(\beta\text{-N-Glc})_2$ | glucose | 4~6% |
| | | $A_{1d}$ | ? | ? | Trace |
| | | $A_{1e}$ | ? | ? | Trace |

$A_{lc}$ is produced non-enzymatically through two reaction steps. In the first reaction, a so-called labile $A_{lc}$ (l-$A_{lc}$) is produced, a part of which reverts to glucose and hemoglobin by a reversible reaction. On the other hand, the second reaction is an irreversible reaction and yields stable-$A_{lc}$ (s-$A_{lc}$).

$HbA_1$, $A_{lc}$, s-$A_{lc}$ and the like are used as indications of diabetes but it is preferable to measure stable-$A_{lc}$ (s-$A_{lc}$) as a more accurate indication.

As methods for separating glycosylated hemoglobin, hemoglobin, and hemoglobin derivatives, there are many methods in which they are separated on the basis of the difference of their electrical properties. Such methods include electrophoretic methods, ion-exchange chromatographic methods, etc. There are also methods based on high-performance liquid chromatography.

As methods for separating s-$A_{lc}$ from l-$A_{lc}$ and measuring the same, there are two methods, i.e., (1) a method in which l-$A_{lc}$ is previously removed by pretreatment, and (2) a method in which s-$A_{lc}$ is separated from l-$A_{lc}$ and detected chromatographically by the use of a separating column.

As the method in which l-$A_{lc}$ is removed by pretreatment, there are methods in which erythrocytes are incubated with physiological saline or a buffer solution containing semicarbazide and aniline (P. A. Svendsen, et al., Diabetologia, 19, 130 (1980); and D. M. Nathan, et al., Claim. Chem., 28, 512 (1982)). These methods require a troublesome pretreatment or are so poor in rapidity that treatment requires 30 minutes to 4 hours. Commercially available instruments (or apparatus) for exclusive use have an on-line l-$A_{lc}$ removing mechanism. It has been reported that the treatment time is reduced by adding a commercially available l-$A_{lc}$ removing reagent to blood and heating the resulting mixture at 50° C. for 1 to 2 minutes (Takahashi et al., Nippon Rinsho Kensa Jidoka Gakkai Kaishi, 12, 133 (1987)). Such a heating treatment is, however, disadvantageous in that it denatures protein to cause precipitation, so that piping or a filter is clogged.

On the other hand, as the method in which s-$A_{lc}$ is separated from l-$A_{lc}$ by the use of a separation column, there are, for example, a method using a packing material consisting of silica as base material and a carboxyl group as ion-exchange group, and a method using a packing material consisting of a polyvinyl alcohol type porous resin. Commercially available instruments for exclusive use also permit separation of s-$A_{lc}$ from l-$A_{lc}$.

In the method using a packing material consisting of silica as base material and a carbonyl group as ion-exchange group, a long time of about 20 minutes is required for separating hemoglobin into components $A_{la}$, $A_{lb}$, HbF, l-$A_{lc}$, s-$A_{lc}$ and $HbA_0$ (Jap. Pat. Appln. Kokai (Laid-Open) No. 63-75558).

In the method using a packing material consisting of a polyvinyl alcohol type porous resin, a long time of about 60 minutes is required for separating hemoglobin into components $A_{Ia}$, $A_{Ib}$, HbF, l-$A_{Ic}$, s-$A_{Ic}$ and HbA$_0$ (Hoshino et al., "Collection of the Substances of Lectures to the 31th Japan Liquid Chromatography Society", No. 29, 175 (1988)).

In another method which uses a vinyl alcohol type copolymer as a packing material, l-$A_{Ic}$, s-$A_{Ic}$ and HbA$_0$ are separated from each other in about 25 minutes. This method, however, has not shed light on components $A_{Ia}$, $A_{Ib}$ and HbF (Jap. Pat. Appln. Kokai (Laid-Open) No. 60-213863).

Details of such packing materials have not been clearly reported. It seems that since the particle size of the packing materials and their physical properties such as specific surface area, exchange capacity, etc. have not been made the most suitable, separation of components from each other is not complete or requires a long time.

In the case of a conventional glycosylated hemoglobin analyzer, it takes about 3.5 minutes to separate hemoglobin into five components $A_{Ia}$, $A_{Ib}$, HbF, $A_{Ic}$ and HbA$_0$ and it takes 8 minutes to separate hemoglobin into six components $A_{Ia}$, $A_{Ib}$, HbF, l-$A_{Ic}$, s-$A_{Ic}$ and HbA$_0$ (Takahashi et al., Japan Rinsho Kensa Jidoka Gakkai Kaishi, 12, 133 (1987)). Hemoglobin of all people is not separated into five or six components because $A_{Ia}$, $A_{Ib}$, HbF or the like is not detected in blood of some people because of low content thereof, and other hemoglobin derivatives are contained in blood of other people. In the present specification, the terms "5-components analysis" and "6-components analysis" are used for convenience.

For separating hemoglobin into the above 5 components, there is used a separation column ($\phi$4.6×35 mm) using a silica gel type material. On the other hand, for separating hemoglobin into the above 6 components, there is used a separation column having a different size ($\phi$4.6×120 mm) and using the same material. In both 5-components analysis and 6-components analysis, elution is carried out by a stepwise gradient method in which three eluents are passed through a separating column stepwise. The 5-components analysis and the 6-components analysis are different from each other in a separating column used and the compositions of eluents used. Therefore, the 5-components analysis and the 6-components analysis cannot be carried out in succession. For example, when the 6-components analysis is carried out after the 5-components analysis, the column and eluents should be exchanged and hence troublesome operations are required. Furthermore, after the column exchange, an eluent should be passed through a relief column for about 10 minutes in order to stabilize the column, so that a long time is required for the measurement.

As a packing material packed into such a column, there is usually used a packing material obtained by introducing a carboxymethyl group as functional group into a silica gel with a particle size of about 5 μm as base material.

A separation column prepared by packing a packing material having a particle size of about 5 μm into a $\phi$4.6×35 mm column permits separation of the above 5 components. However, a separation column having this size (length) does not have a sufficient ability to separate 6 components, and a longer separation column having a inside diameter of 4.6 and a length of 120 mm should be used for this separation.

The chromatographic performances (resolution Rs) are improved in proportion to the square root of the column length (the value of resolution Rs is increased). Thus, the larger the column length, the higher the chromatographic performances but the longer a time required for analysis. In addition, the increase of the column length results in a larger pressure drop and affects the life of column, the life of the seal of a pump, etc.

As described above, in the conventional methods, separation of hemoglobin into 6 components $A_{Ia}$, $A_{Ib}$, HbF, l-$A_{Ic}$, s-$A_{Ic}$ and HbA$_0$ requires a long time of 8 to 60 minutes. Thus, the conventional methods are disadvantageous with respect to analysis time.

The conventional methods do not make it possible to carry out two analyses for components, i.e., 5-components analysis (separation of hemoglobin into $A_{Ia}$, $A_{Ib}$, HbF, $A_{Ic}$ and A$_0$) and 6-components analysis (separation of hemoglobin into $A_{Ia}$, $A_{Ib}$, HbF, l-$A_{Ic}$, s-$A_{Ic}$ and HbA$_0$) by using a single separation column. That is, they do not make it possible to carry out the 5-components analysis and the 6-components analysis in succession and are disadvantageous with respect to the simplicity of operations and rapidity.

The above prior arts involve a problem in that it takes a long time to separate stable-$A_{Ic}$ (s-$A_{Ic}$) from other Hb components ($A_{Ia}$, $A_{Ib}$, HbF, l-$A_{Ic}$, HbA$_0$, etc.) and measure the same.

They also involve the following problems. Hemoglobin cannot be separated into 5 components $A_{Ia}$, $A_{Ib}$, HbF, $A_{Ic}$ and HbA$_0$, and into 6 components $A_{Ia}$, $A_{Ib}$, HbF, l-$A_{Ic}$, s-$A_{Ic}$ and HbA$_0$, by using a single separation column and eluents having the same individual compositions, and a separation column and eluents should be exchanged, so that troublesome operations are required. The exchange of the separation column and the eluents requires a long time. The prior arts are not economical.

SUMMARY OF THE INVENTION

An object of this invention is to provide a method for separating stable-$A_{Ic}$ (s-$A_{Ic}$) from other hemoglobin components rapidly by liquid chromatography and quantitating the same rapidly, and an apparatus used therefor.

Another object of this invention is to provide a method for carrying out the above 5-components analysis and 6-components analysis in succession by using the same column and the same one or more eluents, and an apparatus used therefor.

For achieving the above purposes, the present invention is characterized by a liquid-chromatographic apparatus comprising a separation column packed with a Packing material consisting of a substance having a functional group introduced thereinto, as ion exchanger, a means for injecting a sample into the separation column, a means for passing one or more eluents through the separation column, and a means for detecting hemoglobin, hemoglobin derivatives, or glycosylated hemoglobin, the average particle size of the packing material in dry state being 4 μm or less; or a method for liquid chromatography using said separation column.

The present invention also has the following characteristics. The specific surface area of the packing material in dry state is 10 to 100 m$^2$/g, and the exchange capacity of the packing material per gram thereof based on dry basis is 0.1 to 1 meq.

The functional group is a carboxyl group. In addition, one or more buffer solutions having a pH of 5.0 to 7.0 are used as eluents.

Furthermore, a liquid-chromatographic system is constituted which makes it possible to carry out different analysis (e.g. 5-components analysis and 6-components analysis) in succession.

DETAILED DESCRIPTION OF THE INVENTION

Figure 3:
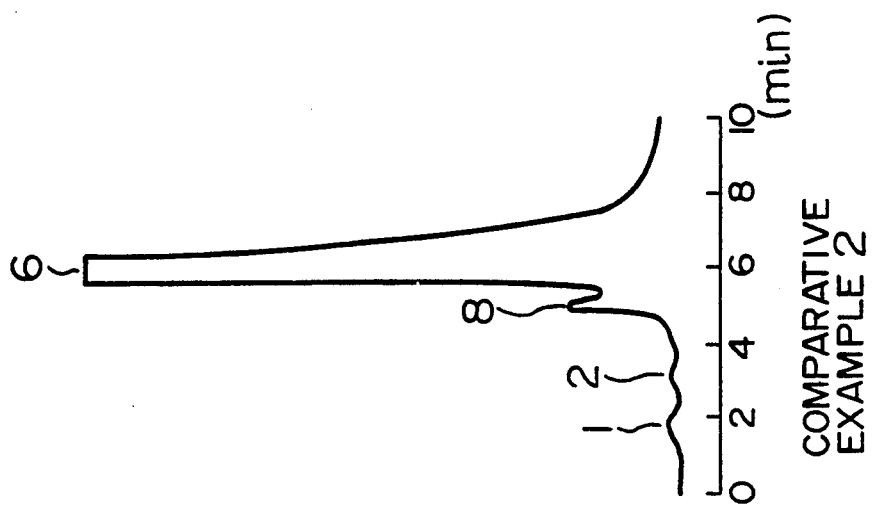
FIG. 3 is a chromatogram obtained in Comparative Example 2.

The chromatographic performances of a separation column can be improved by adjusting the average particle size of a packing material in dry state to as small as 4 μm or less, and there can be used a column which is shorter to that extent. Therefore, the analysis time can be reduced by improving the chromatographic performances.

Packing materials are classified into inorganic polymer packing materials and organic polymer packing materials, according to starting materials. As the inorganic polymer packing materials, those comprising silica gel as base material are widely used.

Even by decreasing the particle diameter, silica gel is resistant because of its properties. On the other hand, in the case of organic polymer packing materials, when the pressure drop of a column is increased by decreasing particle diameter, the packing material is deformed by pressure, so that the chromatographic performances are deteriorated. The deterioration of the chromatographic performances is due to, for example, a change of the packed state of the packing material in the column which is caused by the deformation of the packing material by pressure.

When physical properties such as specific surface area and pore size of a packing material are definite, the pressure drop of a column is increased in inverse proportion to the square of the particle diameter. Therefore, particularly in the case of organic polymer packing materials, it is necessary to improve the pressure resistance, i.e., the mechanical strength, of the packing material itself and reduce the pressure drop of a column (namely, enhance the permeability).

In the present invention, there has been proposed a packing material for analyzing glycosylated hemoglobin which is excellent in chromatographic performances, pressure resistance (mechanical strength) and permeability, and there have been clarified preferable ranges of the particle diameter of a packing material necessary for a high-performance separation column and its physical properties such as specific surface area, the kind of a functional group, the amount of the functional group (i.e., exchange capacity) modified etc.

The separation column used in the analytical method and apparatus of the present invention is superior to conventional columns in resolution, pressure resistance, permeability and the like, because it uses a packing material whose physical properties have been made the most suitable. Because of this superiority in resolution, a shorter column can be used and the analysis time can be reduced. In addition, the above-mentioned 5-components analysis and 6-components analysis can be carried out by the use of a single column by changing the composition(s) of eluent(s) or elution conditions (the kind(s) of eluent(s) need not be changed). Furthermore, because of the superiority in permeability and pressure resistance, said separation column can be used stably for a long period of time.

Therefore, the method and apparatus for analyzing glycosylated hemoglobin of this invention using such a separation column permit rapid, stable and easy (simple) analysis of glycosylated hemoglobin.

Embodiments of the present invention are explained below with reference to the drawings.

As the separation column used in this invention, there can be exemplified columns packed with a packing material of an inorganic or organic substance modified with a functional group, which has an average particle size in dry state of 4 μm or less, a specific surface area of 10 to 100 m$^2$/g and an exchange capacity of 0.1–1 meq/g. As the separation column used in this invention, various ones can be exemplified, though columns packed with a packing material modified with at least one carboxyalkyl group are preferable and columns packed with a packing material modified with at least one carboxymethyl group are more preferable. A method of introducing carboxyalkyl group into an inorganic and organic substance is according to conventional method (Jap. Pat. Appln. Kokai (Laid Open) No. 59-232102).

As the packing material, those comprising an inorganic or organic substance as a base material are used. As the substance, there can be used those generally used for analyzing glycosylated hemoglobin, hemoglobin, etc. by a liquid chromatography. The organic substance includes, for example, methacrylate polymers, vinyl alcohol polymers, styrene-divinylbenzene polymers, etc.

As to the particle size of the packing material, attainment of a desired particle size was confirmed by taking a scanning electron micrograph of the inorganic or organic substance, or measuring the particle size by the Coulter counter method. The specific surface area of the packing material was measured by the BET method. The exchange capacity of the packing material was measured according to a conventional method.

As a column used in this invention, it is preferable to use a cylindrical column having an inside diameter of 1 to 8 mm and a length of 20 cm or less, preferably a cylindrical column having an inside diameter of 1 to 6 mm and a length of 2 to 10 cm.

As a method for packing the packing material into the column, any conventional method may be used so long as it permits uniform packing and control of the packing rate. The control of the packing rate is conducted, for example, by increasing the flow rate of a solvent supplied during packing from the flow rate at the beginning of packing, with the lapse of time.

A liquid chromatography is carried out by adsorbing glycosylated hemoglobin, hemoglobin, and/or derivatives thereof on the separating column, and then passing one or more eluents therethrough to separate glycosylated hemoglobin, etc.

As the eluent(s), any eluent(s) usually used for analyzing glycosylated hemoglobin by a liquid chromatography may be used so long as is or they are buffer solution(s) having a pH of 5.0 to 7.0. There can be used, for example, buffer solutions containing sodium acetate, sodium phosphate, potassium phosphate, etc., and solutions containing salts such as sodium chloride, sodium sulfate, etc. Urea or guanidine may be added to them. In addition, organic solvents such as acetonitrile, ethanol, methanol, mercaptoethanol, etc. may be mixed therewith.

The composition(s) of the eluent(s), for example, the concentrations of a buffer, a salt, urea, an organic solvent, etc. and the pH or pHs are need not to be constant in analyzing glycosylated hemoglobin, hemoglobin or the like by a liquid chromatography. For example, they can be varied in the manner of continuous gradient or stepwise gradient. The flow rate of eluent(s) passed also need not to be constant and can be varied continuously or stepwise with the lapse of time.

Glycosylated hemoglobin, hemoglobin and hemoglobin derivatives in an eluate which have been separated by the use of the separation column of this invention can be detected by measuring visible light having a wavelength of 415 nm. Thus, their separation and quantitation can easily be conducted.

The present invention is further illustrated with the following examples, which are not intended to imply any restriction on the invention within the scope of the gist of the invention.

EXAMPLE 1 AND COMPARATIVE EXAMPLES 1 AND 2

In Example 1, there was used a packing material obtained by introducing carboxymethyl groups as functional groups into a methacrylate polymer as base material.

Table 2 shows the results of measuring physical properties and the pressure drop of the packing material of Example 1.

The packing material used in Example 1 had a particle size of $3.5\pm0.5$ $\mu$m, a specific surface area of 20 $m^2/g$ and an exchange capacity of 0.28 meq/g.

A packing material used in Comparative Example 1 was synthesized so as to have substantially the same specific surface area and exchange capacity as in Example 1 and an average particle size of 5 $\mu$m.

A packing material used in Comparative Example 2 is not a porous substance, has no pores physically formed (namely, no macropore), and has a small specific surface area. Its particle size was $3.5\pm0.5$ $\mu$m which was the same as in Example 1. Its specific surface area was 5 $m^2/g$ which was smaller than the specific surface area of the packing material used in Example 1. In Comparative Example 2, carboxymethyl groups were introduced in the same manner as in Example 1. Since the packing material used in Comparative Example 2 had no macropore and a small specific surface area, its exchange capacity was 0.01 meq/g, namely, the amount of carboxymethyl groups modified was small.

Each of the above three packing materials was packed into a column, whereby separation columns were obtained. The packing materials of Example 1 and Comparative Example 1 were individually packed into a stainless steel column having an inside diameter of 4.6 mm and a length of 35 mm. On the other hand, the packing material of Comparative Example 2 was packed into a larger column having an inside diameter of 7.5 mm and a length of 75 mm, because its specific surface area and exchange capacity were small, so that its contact area with a sample was small.

All the packings were conducted by the slurry method. As a solvent in slurry and a solvent for packing, 80 mM potassium phosphate buffer (pH 6.20) was used. The solvent for packing was supplied at a packing pressure of 150 $kg/cm^2$ for 1 hour.

As a specimen, there was used fresh blood of a normal adult which had been collected after addition of sodium ethylenediaminetetraacetate as anticoagulant. The fresh blood was diluted 200 times with a commercially available hemolysin. 20 Microliters of the hemolysate solution thus obtained was used as a sample of measurement.

As eluents, there were used solutions prepared by dissolving monopotassium phosphate ($KH_2PO_4$) and dipotassium phosphate ($K_2HPO_4$) in desalted water to the following concentrations:

| | |
|---|---|
| Solution a: | 33 mM $KH_2PO_4$ |
| | 7 mM $K_2HPO_4$ |
| | pH 6.2 |
| Solution b: | 160 mM $KH_2PO_4$ |
| | 40 mM $K_2HPO_4$ |
| | pH 6.1 |

There was used an experimental arrangement composed of the following: pump: L-6200 type inteligent

TABLE 2

| | Column size | Particle size ($\mu$m) | Specific surface ($m^2/g$) | Exchange capacity (meq/g) | Pressure drop $\Delta P^1$ ($kg/cm^2$) |
|---|---|---|---|---|---|
| Example 1 | $\phi$4.6 × 35 mm | 3.5 ± 0.5 | 20 | 0.28 | 45 |
| Comparative Example 1 | $\phi$4.6 × 35 mm | 5.0 ± 0.7 | 18 | 0.30 | 25 |
| Comparative Example 2 | $\phi$7.5 × 75 mm | 3.5 ± 0.5 | 5 | 0.01 | 40 |

[1]Flow rate of the eluents: 1.0 ml/min.

Pump mfd. by Hitachi Ltd.; injector: injector having a capacity of 20 μl; detector: L-4200 type UV-VIS detector mfd. by Hitachi Ltd.; data processor: L-2500 type data processor mfd. by Hitachi Ltd.

Analysis was carried out at a column temperature of 25° C. and a measuring wavelength of 415 nm. Separation of components was conducted by the following linear gradient method:

Solution a/solution b = 100/0 by volume $\xrightarrow{10 \text{ min}}$ solution a/solution b = 60/40 by volume Flow rate of the eluents: 1.0 ml/min Table 2 shows measured values of the pressure drop ΔP of the columns of Example 1 and Comparative Examples 1 and 2. These values were obtained when the first solution (solution a/solution b=100/0) was passed at a flow rate of 1.0 ml/min.

In Comparative Example 1, the particle size of packing material was as large as 5 μm, so that the value of ΔP was as small as about half the values obtained in Example 1 and Comparative Example 2. From Example 1 and Comparative Example 2, it can be seen that when the particle size was definite, the packing material having a smaller exchange capacity tended to have a smaller ΔP value (Example 1: exchange capacity 0.28 meq/g, ΔP 45 kg/cm$^2$; Example 2: exchange capacity 0.01 meq/g, ΔP 40 kg/cm$^2$).

Figure 2:
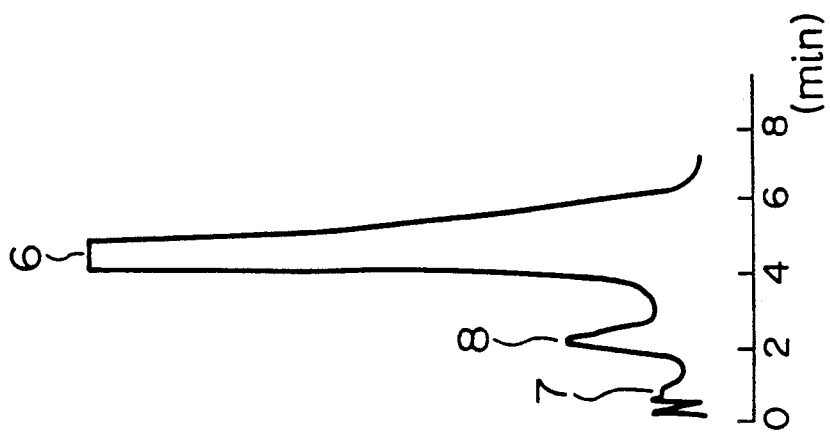
FIG. 2 is a chromatogram obtained in Comparative Example 1.
Figure 1:
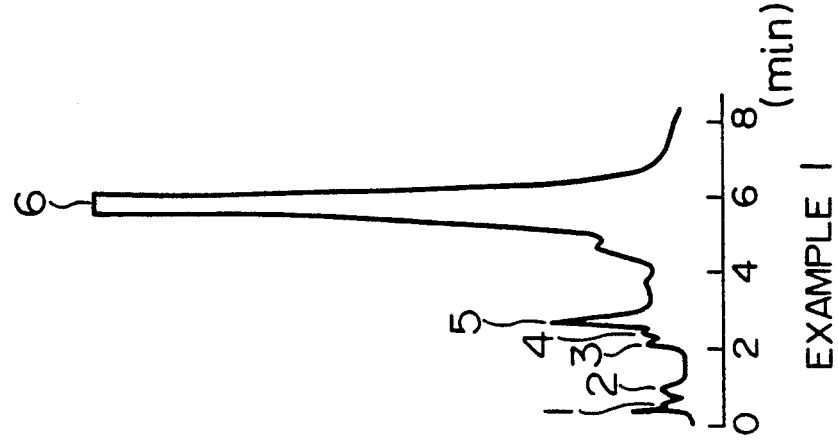
FIG. 1 is a chromatogram obtained in Example 1.

FIGS. 1 to 3 show chromatograms obtained under the above analysis conditions in Example 1 and Comparative Examples 1 and 2, respectively.

In FIG. 1, peak 1 is due to $A_{Ia}$, peak 2 due to $A_{Ib}$, peak 3 due to HbF, peak 4 due to labile-$A_{Ic}$ (l-$A_{Ic}$), peak 5 due to stable-$A_{Ic}$ (s-$A_{Ic}$), and peak 6 due to HbA$_0$.

The individual peaks were identified as follows. Since it is known that various glycosylated hemoglobins can be produced by incubating blood with sugar derivatives, the individual peaks can be identified by confirming the existence of peaks increased in intensity by the incubation with sugar derivatives. Identification as $A_{Ia}$ (peak 1) was conducted by addition of each of fructose-1,6-diphosphate (F-1,6-DP) and glucose-6-phosphate (G-6-P), and identification as $A_{Ib}$ (peak 2) was conducted by addition of pyruvic acid. When glucose was added to blood, followed by incubation, and then a sample was prepared and subjected to measurement, peak 4 was markedly increased in intensity. When measurement was carried out after incubation in physiological saline, peak 4 was decreased in intensity but peak 5 was not changed. From these facts, peak 4 was identified as a peak due to l-$A_{Ic}$ and peak 5 as a peak due to s-$A_{Ic}$. Peak 3 was identified as a peak due to HbF because it showed the same behavior as that of a peak due to the main constituent of umbilical blood (it was eluted at the same position as in the case of the latter).

In FIG. 2 (Comparative Example 1), peak 7 indicates the presence of ($A_{Ia}+A_{Ib}$), peak 8 the presence of (HbF+$A_{Ic}$), and peak 5 the presence of HbA$_c$. The individual peaks were identified in the same manner as in Example 1.

In Comparative Example 1, the average particle size of the packing material used is as large as 5 μm, so that the separation of hemoglobin components was less sufficient as compared with Example 1. That is, the column of Comparative Example 1 did not permit separation of $A_{Ic}$ from HbF. In addition, $A_{Ia}$ and $A_{Ib}$ were eluted at the same position and hence could not be separated from each other.

In FIG. 3 (Comparative Example 2), peak 1 is due to $A_{Ia}$, Peak 2 due to $A_{Ib}$, peak 8 due to (HbF+$A_{Ic}$), and peak 6 due to HbA$_0$. The individual peaks were identified in the same manner as in Example 1.

In Comparative Example 2 in which no macro porous substance was used, the size of the column used was φ7.5 mm×75 mm which was larger than that of the column used in Example 1 (5.7 times the volume of the latter and 2.1 times the length of the latter). In general, separation can be improved by the use of a long column. In Comparative Example 2, $A_{Ic}$ could not be separated from HbF in spite of the use of a relatively large column. Furthermore, the separation between $A_{Ic}$ (peak 8) and HbA$_0$ in Comparative Example 2 was less sufficient than the separation between s-$A_{Ic}$ (peak 5) and HbA$_0$ (peak 6) in Example 1.

As described above, the peaks in Comparative Examples 1 and 2 (FIGS. 2 and 3) were broader than the peaks in Example 1 (FIG. 1). In Comparative Examples 1 and 2, the separation of components of hemoglobin was insufficient.

Therefore, the average particle size of packing material in dry state is preferably 4 μm or less. It is more preferably 1 μm to 4 μm, and it is most preferably 2 μm to 4 μm from the viewpoint of the ease of production.

EXAMPLE 2

There was used a packing material obtained by modifying a methacrylate polymer as base material with carboxymethyl groups as functional groups. The packing material of Example 1 listed in Table 2 was further classified to obtain a packing material having an average particle size of 3.2 μm. This packing material had a particle size of 3.2±0.4 μm, a specific surface area of 21 m$^2$/g and an exchange capacity of 0.28 meq/g.

The packing material after the classification was packed into a stainless steel column having an inside diameter of 4.6 mm and a length of 35 mm, and the column packed with the packing material was used as a separation column. The packing was conducted by the slurry method. As a solvent in slurry and a solvent for packing, 80 mM potassium phosphate buffer (pH 6.20) was used. The solvent for packing was supplied at a packing pressure of 150 kg/cm$^2$ for 1 hour.

Using the above-mentioned separating column, glycosylated hemoglobin and hemoglobin were analyzed by a high-performance liquid chromatography.

As a specimen, there was used fresh blood of a normal adult which had been collected after addition of sodium ethylenediaminetetraacetate as anticoagulant. The blood was diluted in 200 times with a commercially available hemolysin. Twenty microliters of the hemolysate solution thus obtained was used as a sample for measurement.

As eluents, there were used solutions prepared by dissolving monopotassium phosphate (KH$_2$PO$_4$) and dipotassium phosphate (K$_2$HPO$_4$) in desalted water at the following concentrations:

| | |
|---|---|
| Solution A: | 33 mM KH$_2$PO$_4$ |
| | 7 mM K$_2$HPO$_4$ |
| | pH 6.2 |
| Solution B: | 66 mM KH$_2$PO$_4$ |
| | 14 mM K$_2$HPO$_4$ |
| | pH 6.2 |
| Solution C: | 160 mM KH$_2$PO$_4$ |

-continued

| | |
|---|---|
| 40 mM K$_2$HPO$_4$ | |
| pH 6.1 | |

There was used an experimental arrangement composed of the following: pump: L-6200 type inteligent pump mfd. by Hitachi Ltd.; injector: injector having a capacity of 20 μl; detector: L-4200 type UV-VIS detector mfd. by Hitachi Ltd.; data processor: L-2500 type data processor mfd. by Hitachi Ltd.

Analysis was carried out at a column temperature of 25° C. and a detecting wavelength of 415 nm. Separation of components was conducted by the following stepwise gradient method:

| First solution: | solution A | 0 to 0.2 min |
|---|---|---|
| Second solution: | solution A/solution B = 50/50 | 0.3 to 1.5 min |
| Third solution: | solution C | 1.6 to 1.9 min |
| Fourth solution: | solution A | 2.0 to 3.5 min |
| Flow rate of the eluents: | 1.2 ml/min | |
| Pressure loss ΔP: | 65 kg/cm$^2$ | |

Figure 4:
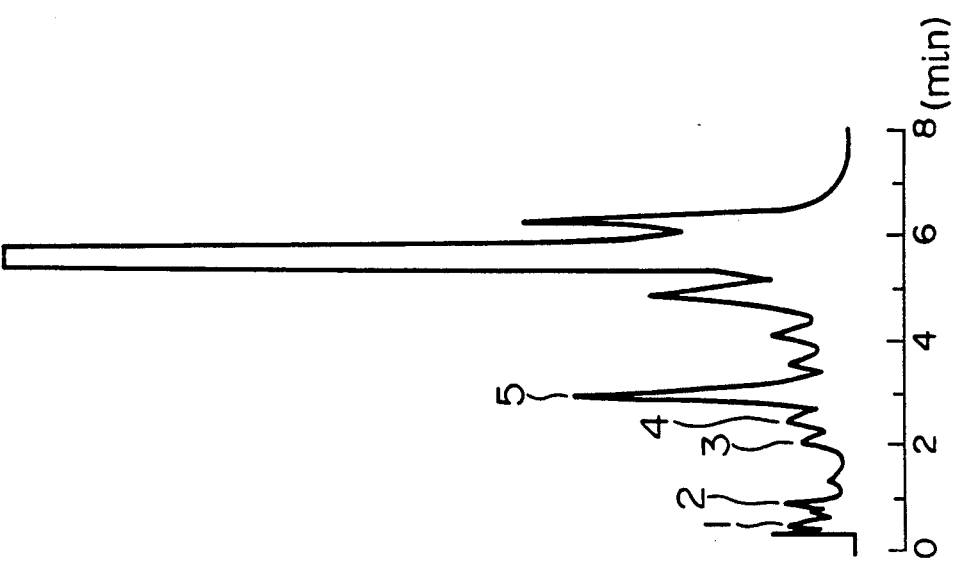
FIG. 4 is a chromatogram obtained in Example 2.

FIG. 4 shows a chromatogram obtained under the above analysis conditions.

Peak 1 is due to A$_{Ia}$, peak 2 due to A$_{Ib}$, peak 3 due to HbF, peak 4 due to labile-A$_{Ic}$ (l-A$_{Ic}$), peak 5 due to stable-A$_{Ic}$ (s-A$_{Ic}$), and peak 6 due to HbA$_0$. The individual peaks were identified by the method described in Example 1.

Thus, hemoglobin in the blood could be separated into 6 components A$_{Ia}$, A$_{Ib}$, HbF, l-A$_{Ic}$, s-A$_{Ic}$ and HbA$_0$, rapidly and satisfactorily.

EXAMPLE 3

Glycosylated hemoglobin and hemoglobin were measured using the same separation column and apparatus as in Example 2. The same sample as in Example 1 was used. Separation of components was conducted by the following stepwise gradient method. Eluents used were the same as in Example 1, and only the program of gradient was different from that used in Example 1.

| First solution: | solution A | 0 to 0.1 min |
|---|---|---|
| Second solution: | solution B | 0.2 to 1.0 min |
| Third solution: | solution C | 1.1 to 1.3 min |
| First solution: | solution A | 1.4 to 2.5 min |
| Flow rate of the eluents: | 1.2 ml/min | |
| Pressure loss of column: | 65 kg/cm$^2$ | |

Other measurement conditions were in accordance with Example 1.

Figure 5:
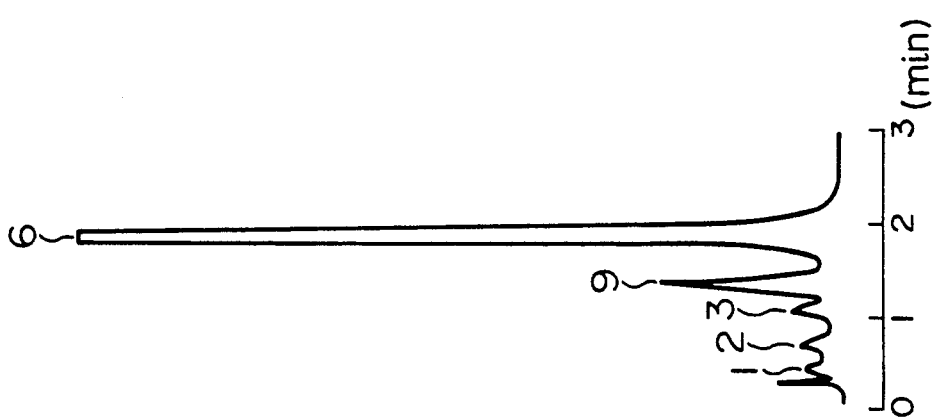
FIG. 5 is a chromatogram obtained in Example 3.

FIG. 5 shows a chromatogram obtained under the above analysis conditions.

Peak 1 is due to A$_{Ia}$, peak 2 due to A$_{Ib}$, peak 3 due to HbF, peak 9 due to A$_{Ic}$ (l-A$_{Ic}$ +s-A$_{Ic}$), and peak 6 due to HbA$_0$.

The individual peaks were identified by the method described in Example 1.

When the method of the present example is employed, l-A$_{Ic}$ and s-A$_{Ic}$ are not chromatographically separated from each other and are detected as a single peak due to A$_{Ic}$. However, the analysis time is still shorter than that in Example 2. In fact, many institutions uses the result of such 5-components analysis as an index to examination and remedy for diabetes.

Thus, the method of the present example was found to permit rapid and satisfactory separation of hemoglobin in blood into 5 components A$_{Ia}$, A$_{Ib}$, HbF, A$_{Ic}$ and HbA$_0$.

EXAMPLE 4

Glycosylated hemoglobin, hemoglobin and hemoglobin derivatives were analyzed using the same separating column and apparatus as in Example 1. The same sample as in Example 1 was used. Separation of components was conducted by the linear gradient method described below. Solution A and solution C in Example 2 were used as eluents.

Solution A/solution B = 100/0 by volume $\xrightarrow{8 \text{ min}}$ solution A/solution C = 50/50 by volume Flow rate of the eluents: 1.0 ml/min
Pressure loss of column ΔP = 55 kg/cm$^2$ Other measurement conditions were in accordance with Example 2.

Figure 6:
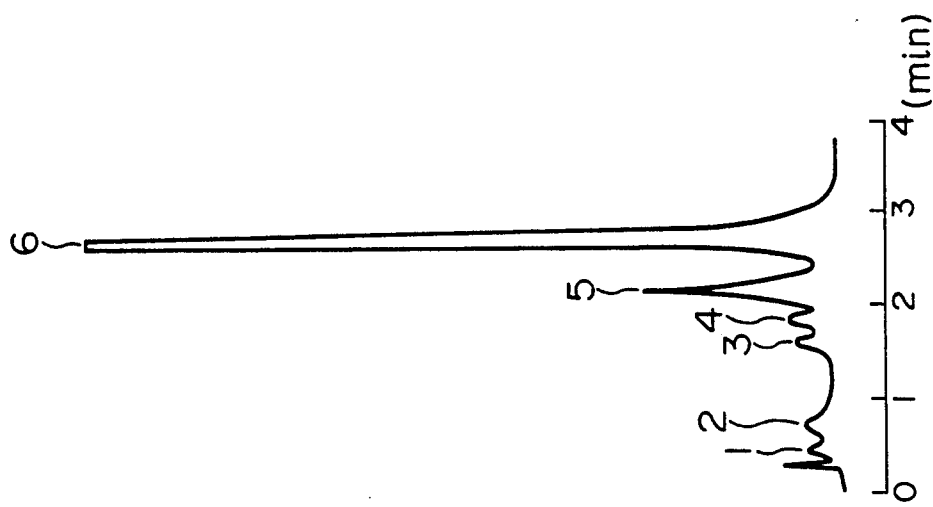
FIG. 6 is a chromatogram obtained in Example 4.

FIG. 6 shows a chromatogram obtained under the above analysis conditions.

Peak 1 is due to A$_{Ia}$, peak 2 due to A$_{Ib}$, peak 3 due to HbF, peak 4 due to l-A$_{Ic}$, peak 5 due to s-A$_{Ic}$, and peak 6 due to HbA$_0$.

The individual peaks were identified by the 1 method described in Example 1.

Peaks other than the above peaks are presumed to be due to the substances described below.

A peak due to hemoglobin having a drug or the like combined (or reacted) thereto appears near a peak due to A$_{Ib}$ (peak 2 in FIG. 6), and a peak due to hemoglobin having aspirin and vitamin B$_6$ combined thereto appears near peaks due to A$_{Ic}$ (peak 4 and peak 5 in FIG. 6). Peaks due to decomposition products of hemoglobin appear between peaks due to A$_{Ic}$ (peak 4 and peak 5 in FIG. 6) and a peak due to HbA$_0$ (peak 6 in FIG. 6). Peaks due to abnormal hemoglobins such as hemoglobin S and hemoglobin C appear after a peak due to HbA$_0$ (peak 6 in FIG. 6).

Thus, the method of the present example permits finer separation of hemoglobin in blood. Therefore, it permits more accurate measurement of s-A$_{Ic}$. Moreover, it makes it possible to obtain information concerning hemoglobin, glycosylated hemoglobin, hemoglobin derivatives and abnormal hemoglobin.

Analysis time required for obtaining such a detailed chromatogram has heretofore been about 1 hour (Hoshino et al. "Collection of the Substances of Lectures to the 31th Japan Liquid Chromatography Society" No. 29 (1988)). The method of the present example makes it possible to carry out analysis in 7 minutes which is one-eighth or less as long as before, by contriving a packing material for a separation column, etc.

More precise analysis can be carried out by making the gradient gentler, though the analysis time becomes longer.

As described above, the column of the present invention makes it possible to carry out the analyses described in Examples 2 to 4 (FIGS. 4 to 6) by the use of the same separation column and the same eluents only by changing the program of gradient.

Therefore, when a plurality of programs of gradient have been previously input, the 6-components analysis, 5-components analysis and multi-components (more than 6 components) analysis (precise analysis) described in Examples 2 to 4 (FIGS. 4 to 6) can be carried out in succession by choosing a program for desired measurement by the flick of a switch.

Thus, 5-components, 6-components, multi-components analyses, etc. can be carried out without exchanging a separation column and eluents, so that there is not required the trouble of exchanging a separation column and eluents. Moreover, since the analyses can be carried out using only one separation column, the cost can be reduced.

A comparison was made between values measured by the analytical method of Example 2 and values measured by the analytical method of Example 3.

As samples, there were used solutions prepared by diluting fresh blood of normal adults and diabetics which contained an anticoagulant added, with hemolysin.

Figure 7:
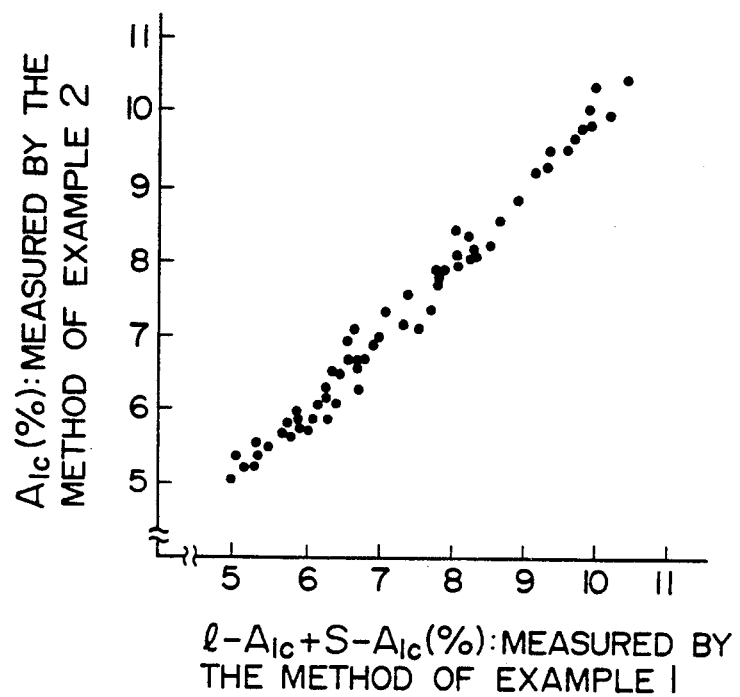
FIG. 7 is a graph showing the correlation between $(1-A_{lc}+s-A_{lc})$ values measured by the method of Example 2 and $A_{lc}$ values measured by the method of Example 3.

FIG. 7 shows measurement results obtained for 60 cases. In FIG. 7, the axis of abscissa refers to the sum of l-$A_{lc}$ concentration (%) and s-$A_{lc}$ concentration (%) which were measured by the method described in Example 2, and the axis of ordinate refers to $A_{lc}$ concentration (%) measured by the method described in Example 3.

The correlation coefficient $\gamma$ between the values measured by the method of Example 2 and the values measured by the method of Example 3 was 0.994. When the value measured by the method of Example 2 was taken as X and the value measured by the method of Example 3 was taken as Y, the correlation was represented by the formula: $Y = 1.034X - 0.310$. Thus, there was very good correlation between the measured values obtained by the two methods.

It can be seen that the methods of Examples thus permit high-precision analysis of hemoglobin in blood. That is, it can be seen that they permit high-precision measurement even when the number of components to be measured is increased as in the case of 6-components analysis.

EXAMPLE 5

Figure 8:
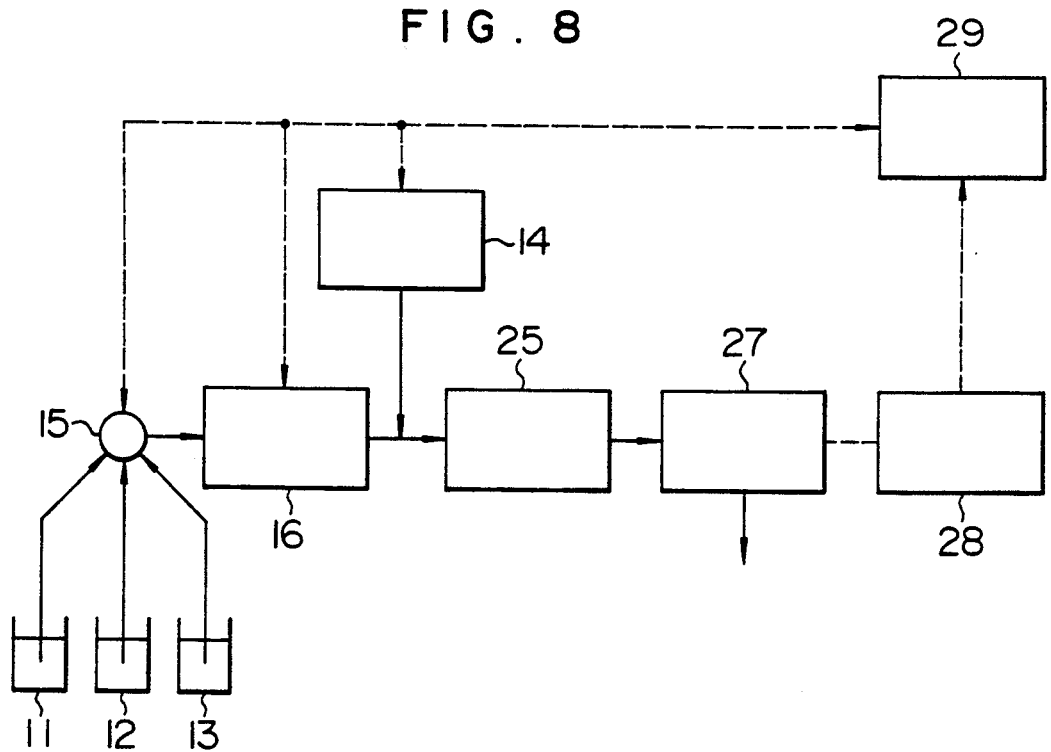
FIG. 8 and FIG. 9 show one embodiment of the analytical apparatus of this invention.
Figure 9:
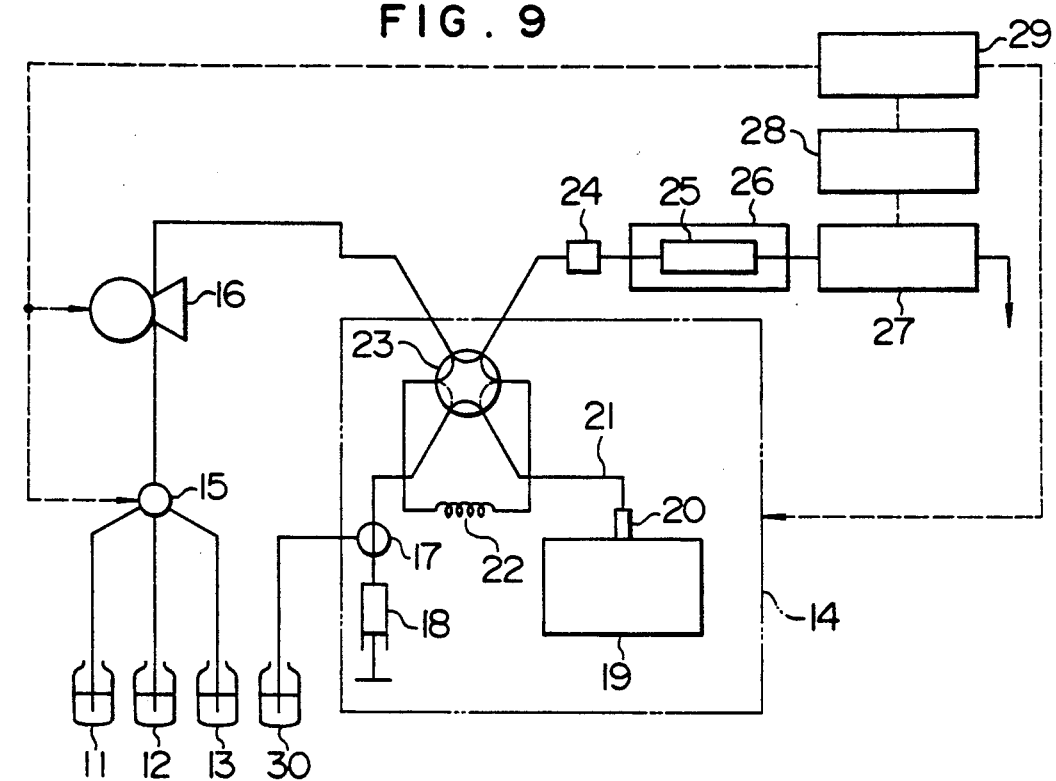

FIG. 8 shows the main system structure of the apparatus of this invention, and FIG. 9 the detailed structure of said apparatus.

As a sample, there was used fresh blood collected after addition of sodium ethylenediaminetetraacetate as anticoagulant. The blood was diluted 200 times with a commercially available hemolysin and set in the sample table 19 of the auto-sampler 14 which are shown in FIG. 8 and FIG. 9. A separation column 25 was used which was the same as the separation column used in Example 2. The column measured 4.6 mm in inside diameter and 35 mm in length. The temperature of a constant temperature bath for column (an oven) 26 was set at 30° C. As eluents, there were used solution A 11, solution B 12 and solution C 13 which were described in Example 2. In FIG. 8 and FIG. 9, the arrows of solid line indicate the flows of liquids such as the sample and reagents, and the arrows of chain line the flows of signals.

In the case of 5-components analysis (separation of hemoglobin into 5 components $A_{la}$, $A_{lb}$, HbF, $A_{lc}$ and $A_0$), the components were separated by employing the following stepwise gradient:
Solution A: 0 to 0.1 min
Solution B: 0.2 to 1.0 min
Solution C: 1.1 to 1.3 min
Solution A: 1.4 to 2.5 min
Flow rate of the eluents: 1.2 ml/min The sample set in the sample table 19 was introduced into a six-way valve 23 through a suction nozzle 20 and a sample transfer tube 21 by means of a syringe 18, thereafter passed through a filter 24, and then introduced into the separation column 25. The symbol 22 denotes a sample loop. A washing solution 30 was supplied through a three-way valve 17. Solution A 11, solution B 12 and solution C 13 were supplied to the separation column 25 through a three-way solenoid valve 15 by means of a solution transfer pump (inteligent pump) 16. The absorbances of the eluate from the separation column 25 at wavelengths of 415 nm and 690 nm (for measuring the background absorbance) were measured by means of a detector 27.

Under the above gradient conditions, as shown in FIG. 5, hemoglobin could be separated into 5 components $A_{la}$, $A_{lb}$, HbF, $A_{lc}$ and Ab$A_0$ on a 2.5-minute cycle. On the basis of the chromatogram thus obtained, the proportion (percentage) (%) of $A_{lc}$ to the total hemoglobin was calculated by means of a data processor 28.

In the case of 6-components analysis (separation of hemoglobin into 6 components $A_{la}$, $A_{lb}$, HbF, l-$A_{lc}$, s-$A_{lc}$ and Hb$A_0$), hemoglobin was analyzed by employing the following stepwise gradient:

| | |
|---|---|
| Solution A: | 0 to 0.2 min |
| Solution A/solution B = 50/50: | 0.3 to 1.5 min |
| Solution C: | 1.6 to 1.9 min |
| Solution A: | 2.0 to 3.5 min |
| Flow rate of the eluents: | 1.2 ml/min |

When analyzed under the above gradient conditions, hemoglobin could be separated into 6 components $A_{la}$, $A_{lb}$, HbF, l-$A_{lc}$, s-$A_{lc}$ and Ab$A_0$ on a 3.5-minute cycle, as shown in FIG. 4. On the basis of the chromatogram thus obtained, the proportion (percentage) (%) of s-$A_{lc}$ to the total hemoglobin was calculated by means of the data processor 28.

An operation part 29 controls the auto-sampler 14, the solution transfer pump (inteligent pump) 16 and the three-way solenoid valve 15 on the basis of the output of the data processor.

In addition, multi-components (more than 6 components) analysis was carried out by the following linear gradient method:

$$\text{Solution A/solution C} = 100/0 \text{ by volume} \xrightarrow{8 \text{ min}}$$

solution A/solution C = 50/50 by volume

Flow rate of the eluents: 1.0 ml/min

After the analysis, solution A was passed at a flow rate of 1.0 ml/min from 8.1 minutes to 10.0 minutes to return the column to its initial state.

The analysis under the above gradient conditions gave the chromatogram shown in FIG. 6.

EXAMPLE 6

Figure 10:
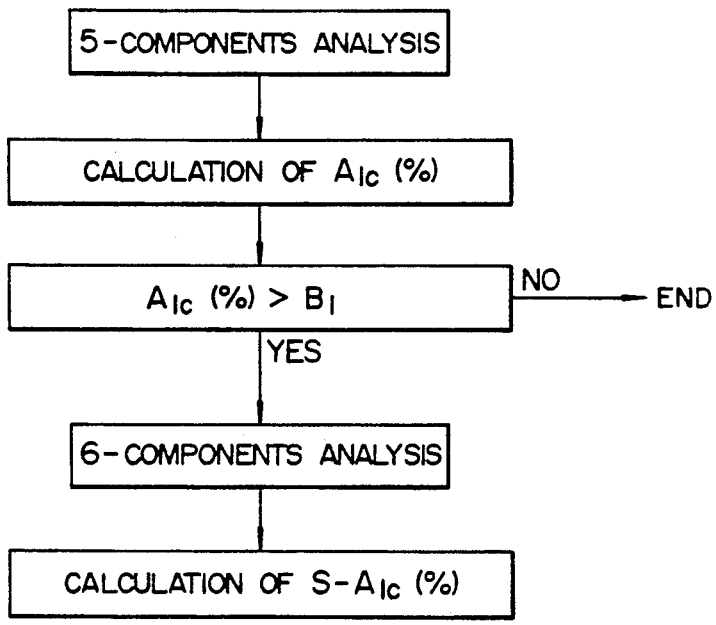
FIGS. 10 to 12 are flow charts of examples of this invention.

FIG. 10 shows one example of flow chart of analysis of glycosylated hemoglobin. The apparatus described in Example 5 was used. The programs of gradient described in Example 5 are referred to as follows. The program of gradient for carrying out 5-component analysis is referred to as program ①, the program of gradient for carrying out 6-components analysis as program ②, and the program of gradient for carrying out multi-components analysis as program ③.

First, 5-components analysis is carried out by employing program ①. As shown in FIG. 5, program ① permits separation of hemoglobin into $A_{Ia}$, $A_{Ib}$, HbF, $A_{Ic}$ and $AbA_0$ on a 2.5-minutes cycle. On the basis of the chromatogram thus obtained, the percentages of components are calculated. In the case of a sample in which the percentage (%) of $A_{Ic}$ is less than a certain value ($B_1$), the analysis is finished. On the other hand, only a sample in which the percentage (%) of $A_{Ic}$ exceeds the certain value ($B_1$) is subjected to 6-components analysis.

Signals indicating the numbers of samples requiring 6-components analysis are transmitted to the auto-sampler 14 from the operation part 29.

At the same time, the signals are transmitted from the operation part 29 to the three-way solenoid valve 15 and the inteligent pump 16 in which the flow rate and the like can be controlled by a command, whereby program 2 for 6-components analysis is carried out. In this case, it is necessary to change the mixing ratio of eluents, their switching times, their flow rate, etc. The $B_1$ value can freely be determined using $\bar{x}+SD$ ($\bar{x}$: average value, SD: standard deviation), $\bar{x}+2SD$, etc.

Using program ②, hemoglobin can be separated into 6 components $A_{Ia}$, $A_{Ib}$, HbF, $1-A_{Ic}$, $s-A_{Ic}$ and $AbA_0$ on a 3.5-minutes cycle.

$A_{Ic}$ is known to be produced non-enzymatically through two reaction steps. First, glucose and hemoglobin are combined to each other through an aldimine linkage to form $1-A_{Ic}$. Next, the aldimine linkage is gradually changed to ketoamine linkage by Amadori rearrangement, resulting in irreversible formation of $s-A_{Ic}$. The formation rate of $1-A_{Ic}$ is as rapid as about 60 times the formation rate of $s-A_{Ic}$, and a large portion of $1-A_{Ic}$ dissociates into glucose and hemoglobin. The amount of $s-A_{Ic}$ is not changed by physiological factors such as meal, but the amount of $1-A_{Ic}$ is rapidly increased by a meal or the like. Therefore, measurement of $s-A_{Ic}$ permits more accurate screening with respect to diabetes than does measurement of $A_{Ic}$.

In the method of the present example, 5-components analysis is carried out for all samples and the percentage of $A_{Ic}$ in each sample is calculated. From the $A_{Ic}$ value thus obtained, there is judged in the operation part 29 whether 6-components analysis is necessary or not (whether $A_{Ic}$ is larger than $B_1$ or not), and only samples satisfying the inequality $A_{Ic} > B_1$ are subjected to 6-components analysis. In said method, it is possible to subject all the samples set in the auto-sampler 14 to 5-components analysis and then subject samples among them which satisfy the inequality $A_{Ic} > B_1$, to 6-components analysis in one lot. It is also possible to repeat 5-components analysis on each sample followed by 6-components analysis which is carried out when the sample satisfies the inequality $A_{Ic} > B_1$.

EXAMPLE 7

Figure 11:
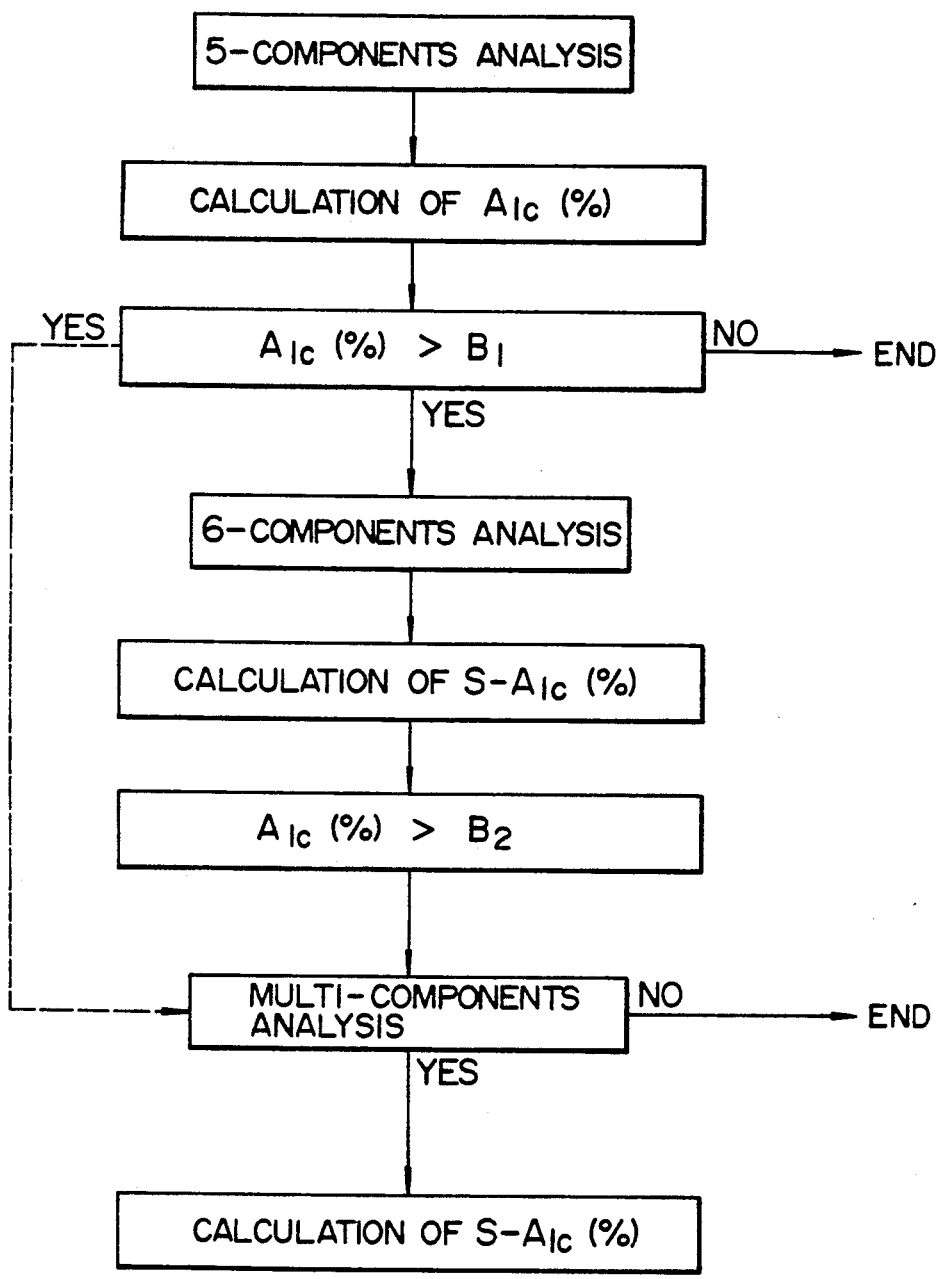

FIG. 11 shows one example of flow chart of analysis of glycosylated hemoglobin.

An apparatus used is the same as in Example 5.

First, 5-components analysis is carried out and the percentage of $A_{Ic}$ is calculated. Then, whether $A_{Ic}$ is larger than $B_1$ or not is judged, and only samples satisfying the inequality $A_{Ic} > B_1$ are subjected to 6-components analysis, after which the percentage of $s-A_{Ic}$ is calculated. Whether $s-A_{Ic}$ is larger than $B_2$ or not is similarly judged, and only samples satisfying the inequality $s-A_{Ic} > B_2$ are subjected to multi-components (more than 6 components) analysis.

Whether samples satisfy the inequality $A_{Ic} > B_1$ of the inequality $s-A_{Ic} > B_2$ is judged in the operation part 29, and signals indicating the numbers of samples satisfying this condition are transmitted to the auto-sampler. A signal of carrying out gradient program 2 or 3 is transmitted to the three-way solenoid valve 15 and the inteligent pump 16 to change the mixing ratio of eluents, their flow rates, their switching times, etc.

The multi-components analysis may be carried out immediately after the 5-components analysis.

EXAMPLE 8

Figure 12:
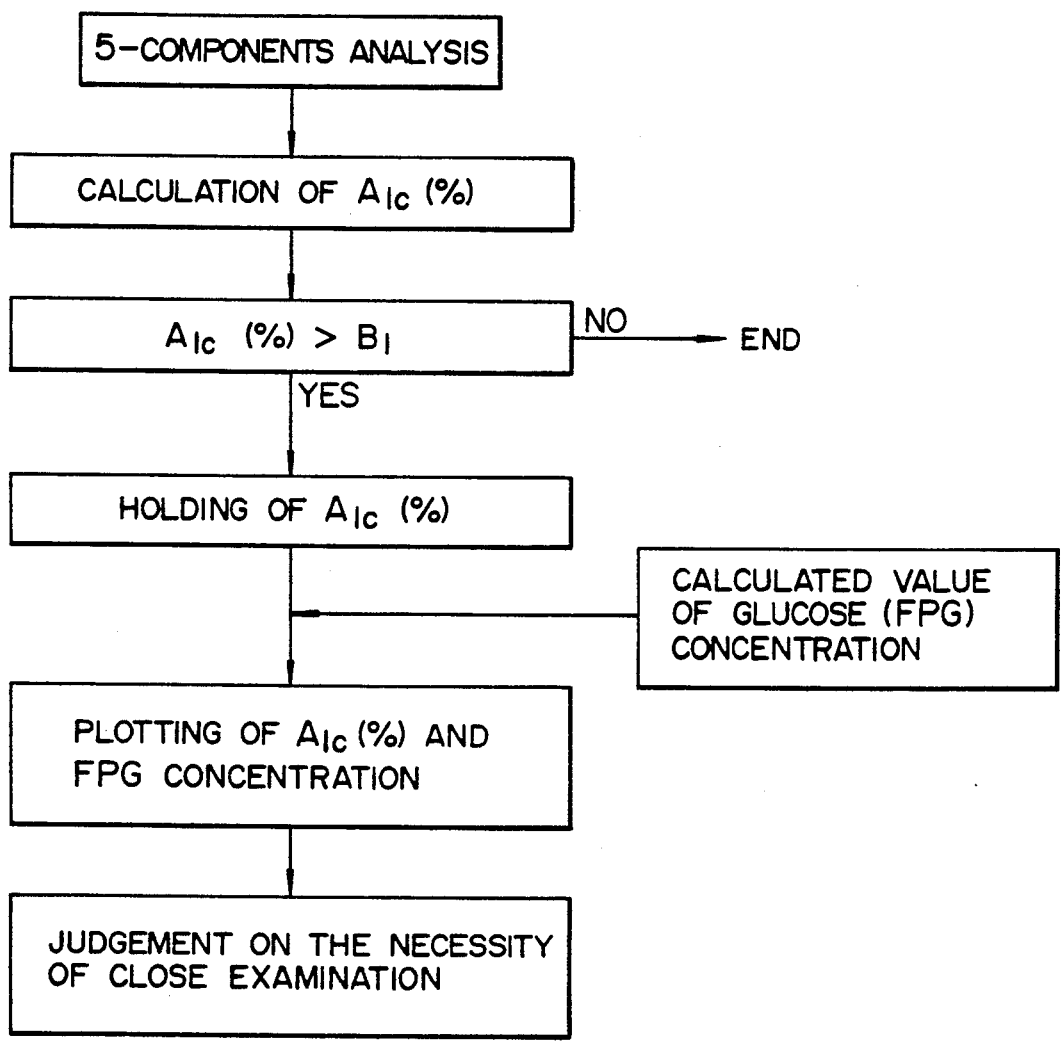

FIG. 12 shows a flow chart of analysis of glycosylated hemoglobin.

In the present example, whether close examination is necessary or not is judged from the measured value of glycosylated hemoglobin and glucose concentration.

Japan Comprehensive Health-Screening Medical Society has taken its recommendation described below. Glucose tolerance screening is conducted by combination of fasting blood sugar level (FPG) and $A_{Ic}$, and persons who have undergone to screening and satisfy the conditions described below are judged to be persons requiring close examination, and subjected to 75 g glucose tolerance test (75 g GTT).

| Conditions: | | |
|---|---|---|
| (1) | FPG: | 140 mg/dl or more |
| (2) | $A_{Ic}$: | $\bar{x}$ + 2SD or more |
| (3) | FPG: | 110–140 mg/dl |
| | $A_{Ic}$: | $\bar{x}$ + 1SD or more |

Figure 13:
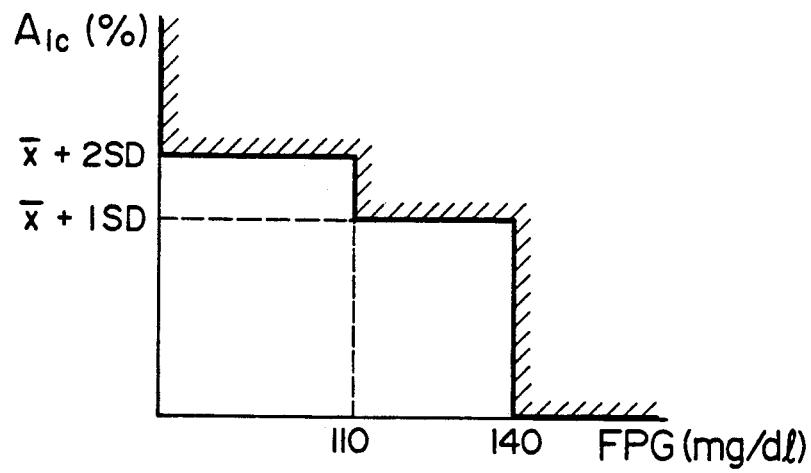
FIG. 13 shows conditions of glucose tolerance screening.

FIG. 13 shows the relationship between FPG and $A_{Ic}$ in glucose tolerance screening. Persons who have undergone the screening and correspond to values plotted at the positions in the shadowed range, require close examination.

First, 5-components analysis is carried out and the percentage of $A_{Ic}$ is calculated. Whether the percentage of $A_{Ic}$ is more than $B_1$ or not is judged. For example, $\bar{x}+SD$, $\bar{x}+2SD$, or the like can be employed as $B_1$. Only when the percentage of $A_{Ic}$ is larger than $B_1$, the value of $A_{Ic}$ is held and the calculated value of glucose (FPG) concentration and the percentage of $A_{Ic}$ are plotted on the graph shown in FIG. 13, whereby whether close examination is necessary or not is judged. The plotting on the graph may be conducted in an operation part.

Figure 14:
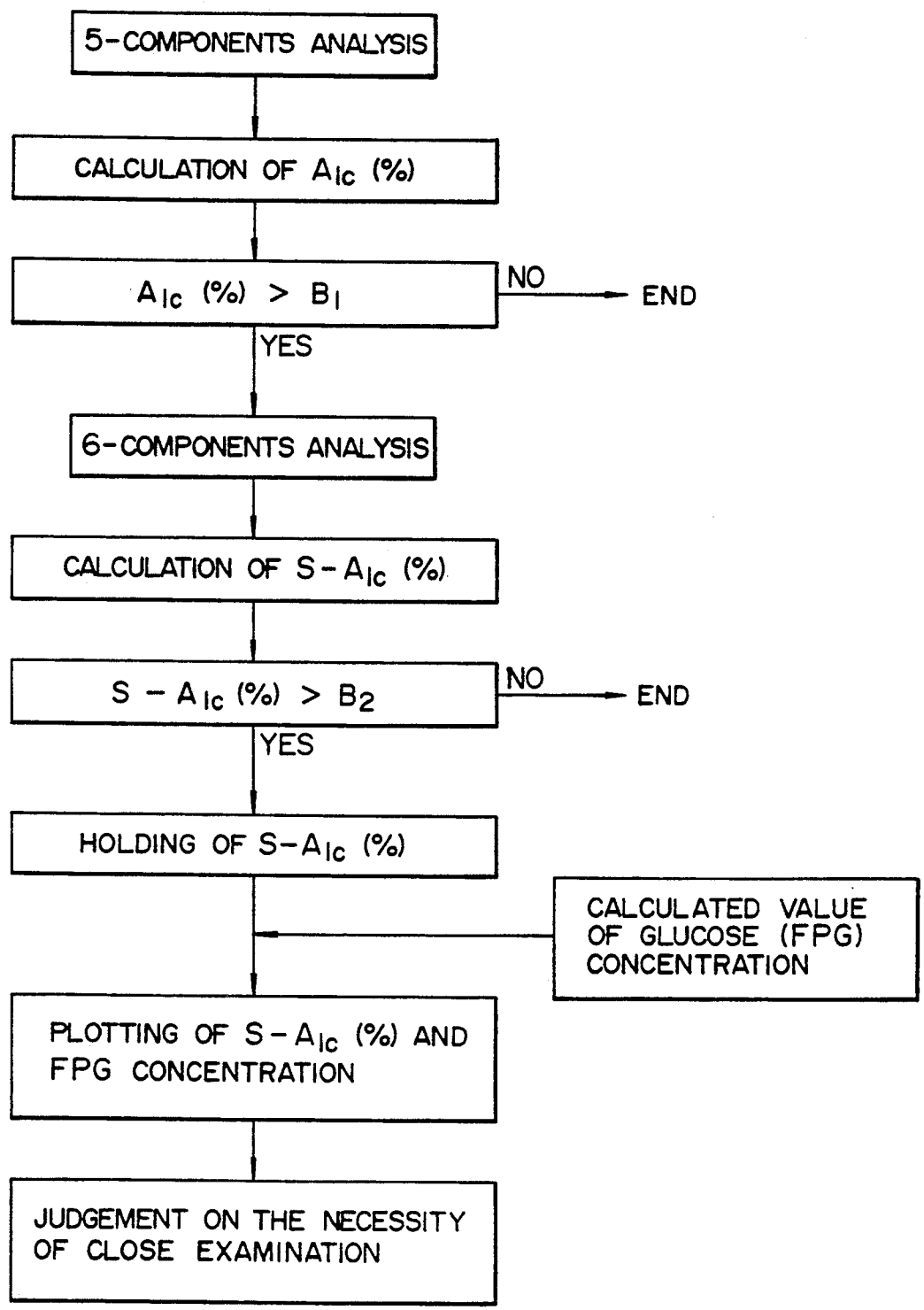

FIG. 14 shows a flow chart for judging whether close examination is necessary or not, from the percentage of $s-A_{Ic}$ and fasting blood sugar level (FPG).

EXAMPLE 9

Figure 15:
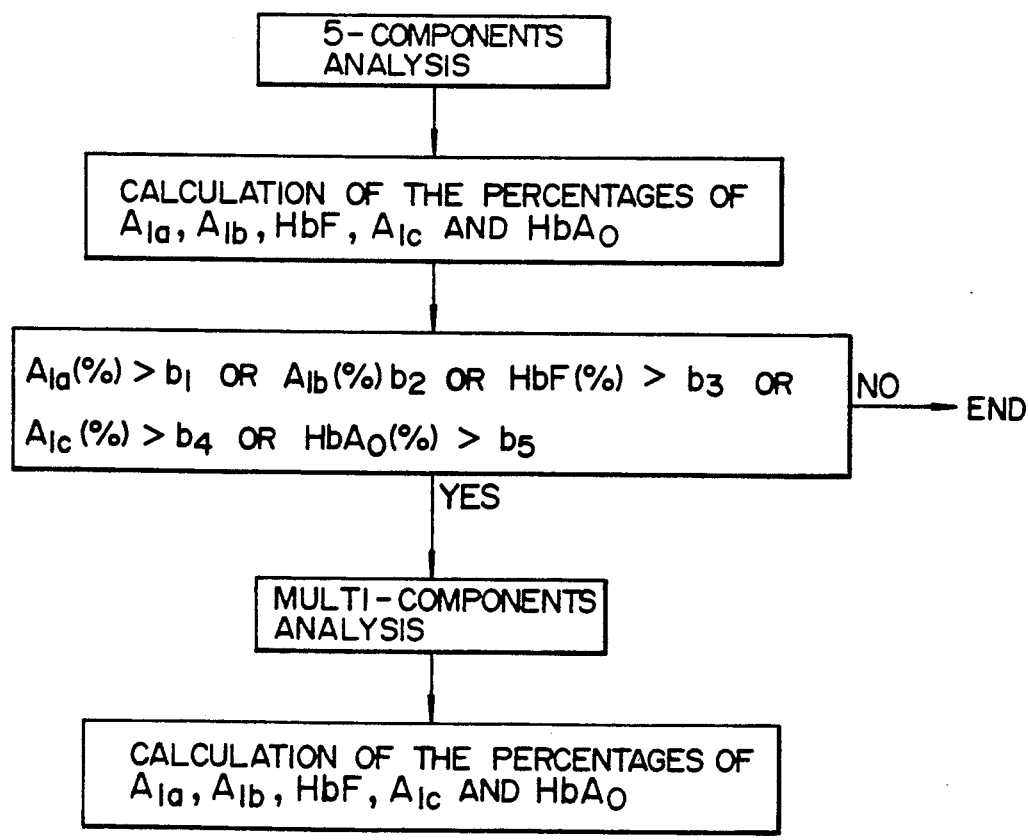
FIG. 14 and FIG. 15 are flow charts of examples of this invention.

FIG. 15 shows one example of flow chart of analysis of glycosylated hemoglobin.

First, 5-components analysis is carried out using the system described in Example 5, and the percentages of $A_{Ia}$, $A_{Ib}$, HbF, $A_{Ic}$ and $AbA_0$ are calculated. Next, there is judged whether the percentage of a certain component among $A_{Ia}$, $A_{Ib}$, HbF, $A_{Ic}$ and $AbA_0$ is larger than a certain value (when it is larger than a certain value, there is a possibility of an abnormal pattern). Multicomponents analysis is carried out only when the percentage of a certain component (which can be properly determined depending on the purpose of examination) among fractions obtained by fractionating hemoglobin is larger than a certain value, and whether an abnormal hemoglobin Pattern is formed or not is checked.

As described above, the method of the present example makes it possible to carry out 5-components analysis, 6-components analysis, multi-components (more than 6 components) analysis, etc. in succession by the use of the same column and the same eluents only by changing the program of gradient. Therefore, it permits reduction of the time required for analysis. It can be automated. It is convenient, because the column and the eluent need not be exchanged.

In addition, whether a closer analysis is carried out or not is judged from the measured value (percentage) of a component $A_{lc}$ or $s-A_{lc}$ obtained by fractionating hemoglobin, and the closer analysis is carried out when needed, whereby more accurate measured values can be obtained. There are, for example, the following courses: 5-components analysis→6-components analysis; 6-components analysis→multi-components analysis; 5-components analysis→multi-components analysis; etc.

More accurate examination and treatment for diabetes can be conducted by taking such a course.

COMPARATIVE EXAMPLE 3

There was used a packing material obtained by modifying a methacrylate polymer as base material with carboxymethyl groups as functional groups.

Physical properties of said packing material were measured to be as follows: particle size $8.0 \pm 1.6$ μm, specific surface area 25 m$^2$/g, exchange capacity 0.30 meq/g.

The packing material was packed into a stainless steel column having an inside diameter of 4.6 mm and a length of 120 mm. The packing was conducted by the slurry method. As a solvent in slurry and a solvent for packing, 80 mM potassium phosphate buffer (pH 6.20) was used, and the solvent for packing was supplied at a packing pressure of 100 kg/cm$^2$ for 1 hour.

The same sample and experimental arrangement as in Example 1 were used.

As eluents, there were used solutions prepared by dissolving monosodium phosphate (NaH$_2$PO$_4$.2H$_2$O) and/or sodium chloride (NaCl) in desalted water to the concentrations described below. The pH's of the solutions were adjusted with HCl.

Solution α: 30 mM NaH$_2$PO$_4$.2H$_2$O (pH 5.5)

Solution β: 30 mM NaH$_2$PO$_4$.2H$_2$O + 300 mM NaCl (pH 5.5)

Figure 16:
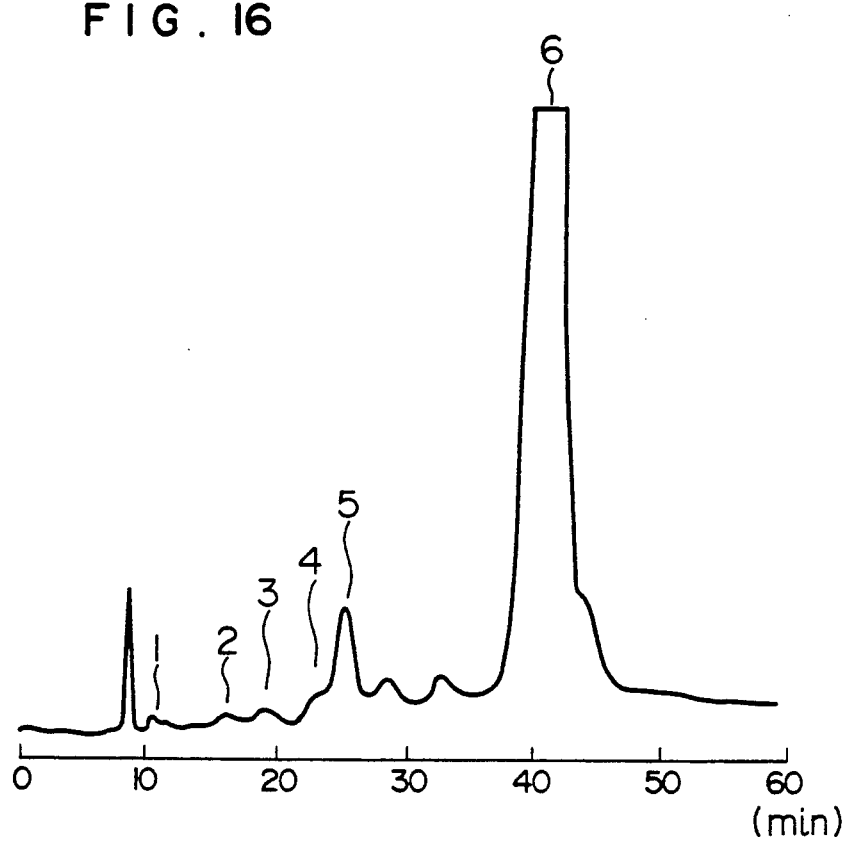
FIG. 16 shows a chromatogram obtained in Comparative Example 4.

Separation of components was conducted by the following linear gradient method:

Solution α/solution β = 100/0 by volume $\xrightarrow{10\ min}$ solution α/solution β = 70/30 by volume Flow rate of the eluents: 1.0 ml/min FIG. 16 shows a chromatogram obtained by the use of the packing material of Example 4 under the above analysis conditions.

In FIG. 16, peak 1 is due to $A_{la}$, peak 2 due to $A_{lb}$, peak 3 due to HbF, peak 4 due to labile-$A_{lc}$ (l-$A_{lc}$), peak 5 due to stable-A (s-$A_{lc}$), and peak 6 due to HbA$_0$.

When the packing material having a particle size of 8 μm was used, it took about 50 minutes to separate hemoglobin into the 6 components $A_{la}$, $A_{lb}$, HbF, l-$A_{lc}$, s-$A_{lc}$ and HbA$_0$. Therefore, in Comparative Example 3, the measurement time is much longer than in Examples of this invention and a large number of samples could not be examined in a short time.

EXAMPLES 10 TO 12 AND COMPARATIVE EXAMPLES 3 AND 4

Packing materials were synthesized so as to have the same specific surface area and exchange capacity as those of the packing material described in Comparative Example 3 (particle size: $8.0 \pm 1.6$ μm, specific surface area: 25 m$^2$/g, exchange capacity 0.30 meq/g) and a particle size of approximately 5 μm, 4 μm, 3.5 μm, or 3 μm. FIG. 3 shows the results of measuring physical properties of these packing materials. From the measured values of particle size, specific surface area and exchange capacity, the packing materials of Comparative Examples 3 and 4 and Examples 10 to 12 can be considered to be packing materials having substantially the same specific surface area and exchange capacity and different particle sizes.

Each of the packing materials of Comparative Example 4 and Examples 10 to 12 was packed into a column having an inside diameter of 4.6 mm and a length of 35 mm, and the columns thus treated were used as separation columns. The packing material of Comparative Example 3 was packed into a column having an inside diameter of 4.6 mm and a length of 120 mm, as described above. The packing of the packing materials of Comparative Example 4 and Examples 10 to 12 into the respective columns was conducted in the sam manner as in Comparative Example 3.

The same experimental arrangement as in Example 1 was used. Standard hemoglobin was used as a sample. As an eluent, there was used a solution prepared by mixing monosodium phosphate (NaH$_2$PO$_4$.2H$_2$O) and sodium chloride (NaCl) to adjust their concentrations to the concentrations described below.

TABLE 3

| | Particle size (μm) | Specific surface area (m$^2$/g) | Exchange capacity (meq/g) |
|---|---|---|---|
| Comparative Example 3 | 8.0 ± 1.6 | 25 | 0.30 |
| Comparative Example 4 | 5.1 ± 0.6 | 18 | 0.28 |
| Example 10 | 3.9 ± 0.5 | 18 | 0.29 |
| Example 11 | 3.5 ± 0.5 | 20 | 0.30 |
| Example 12 | 3.1 ± 0.4 | 23 | 0.30 |

30 mM NaH$_2$PO$_4$.2H$_2$O
100 mM NaCl
pH 5.5

HETP (height equivalent to a theoretical plate) was measured at various flow rates of the above eluent.

Figure 17:
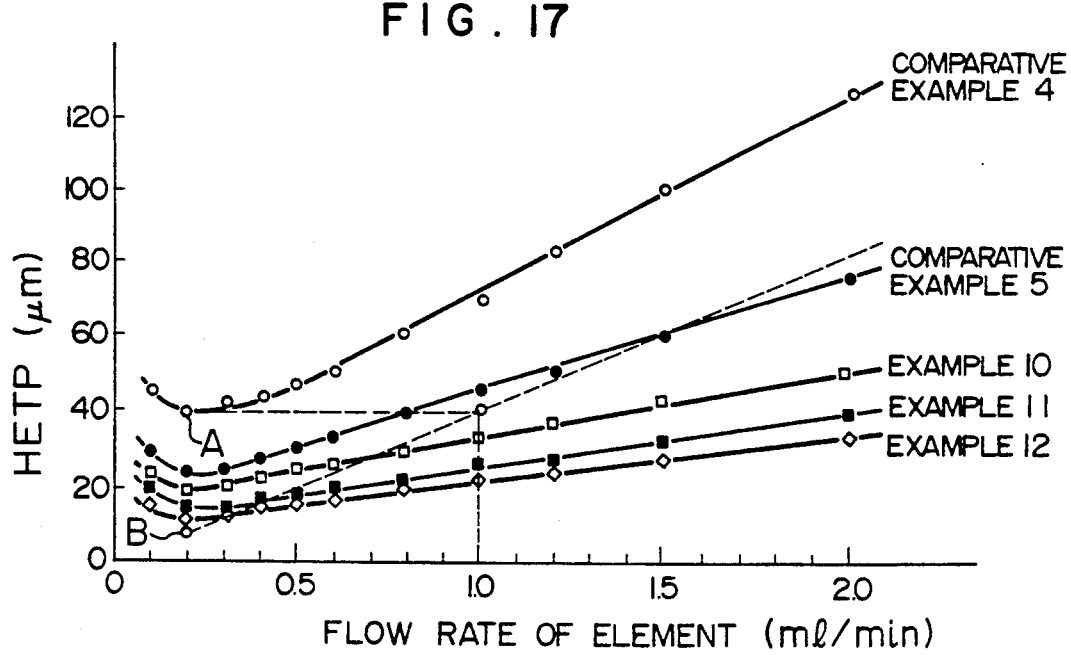
FIG. 17 is a graph showing the relationship between the flow rate of eluent and HETP.

FIG. 17 shows the relationship between HETP and the flow rate of the eluent in each of the columns packed with the packing materials of Comparative Examples 3 to 4 and Examples 10 to 12, respectively.

The smaller the particle size of packing material, the smaller the minimum of HETP, and the smaller the rate of increase in HETP with an increase of the flow rate of the eluent.

HETP is an expression of chromatographic efficiency (chromatographic performances or resolution) in liquid chromatography. The smaller the value of HETP, the sharper a peak which can be obtained.

In FIG. 17, in the region below the straight line (broken line) connecting the point (B) at which the flow rate is the same as that corresponding to the minimum (A) of HETP in Comparative Example 4 and the value of HETP is one-fifth of the minimum (A), with the point (C) at which the value of HETP is the same as the minimum (A) of HETP is Comparative Example 4 and the flow rate is 5 times that corresponding to the minimum (A), the analysis time can be reduced to one-fifth or less while keeping the resolution shown in FIG. 16. In addition, the analysis time can be further reduced by choosing proper elution conditions (for example, by employing a stepwise gradient method).

In the region above the broken line in FIG. 17, the resolution is not sufficient, and $A_{Ic}$ cannot be separated into $l$-$A_{Ic}$ and s-$A_{Ic}$ while reducing the analysis time to one-fifth. Therefore, a longer column should be used for separating $A_{Ic}$ into $l$-$A_{Ic}$ and s-$A_{Ic}$. With an increase of the length of column, the analysis time is increased.

In FIG. 17, the line of Comparative Example 5 (a packing material having a particle size of about 5 $\mu$m) is above the broken line in a conventional flow rate range of 1.0–1.5 ml/min. The higher the flow rate, the higher the pressure applied to the column and the shorter the life of the packing material.

In FIG. 17, in the case of Examples 10, 11 and 12 (packing materials having particle sizes of approximately 4 $\mu$m, 3.5 $\mu$m and 3.0 $\mu$m, respectively), the value of HETP at a flow rate of 1.0 ml/min is below the broken line and analysis for 6 components $A_{Ia}$, $A_{Ib}$, HbF, $l$-$A_{Ic}$, s-$A_{Ic}$ and $AbA_0$ can be carried out without decreasing the life of the packing materials, while reducing the analysis time to one-fifth.

EXAMPLES 11, 13 AND 14 AND COMPARATIVE EXAMPLES 5 AND 6

The relationship between the specific surface area of a packing material and its exchange capacity or HETP is described below.

Figure 18:
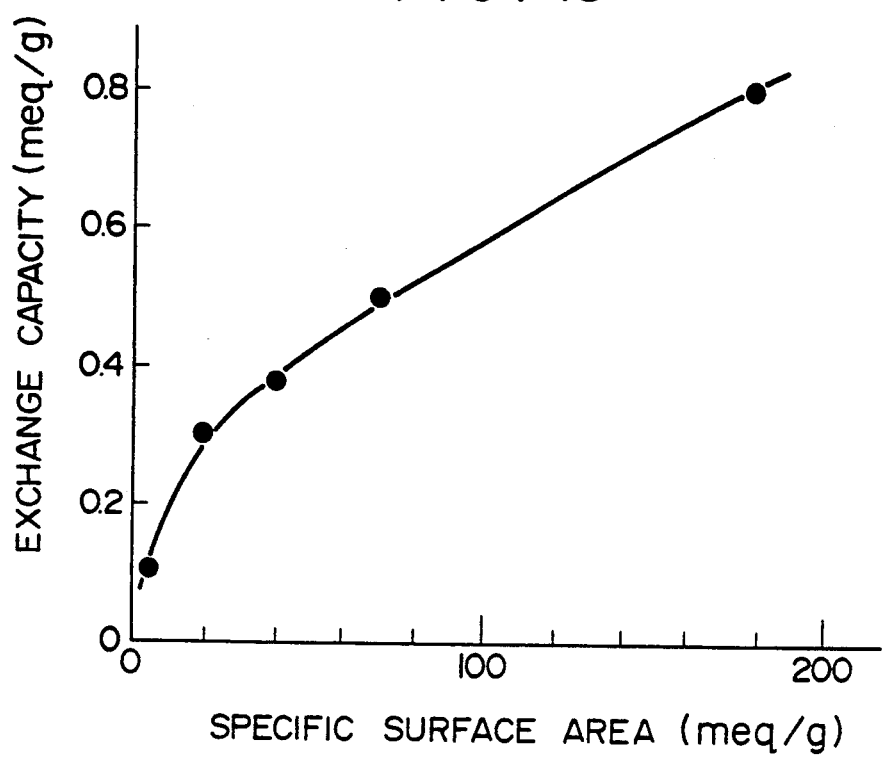
FIG. 18 is a graph showing the relationship between specific surface area and exchange capacity.

Base materials consisting of a methacrylate gel were synthesized so as to have an average particle size of 3.5 $\mu$m and different specific surface areas. Carboxymethyl groups were combined to the base materials under the same conditions. Physical properties of the packing materials thus obtained were checked by measuring their particle size, specific surface area (after the introduction of the functional group) and exchange capacity. FIG. 4 shows the results of measuring the physical properties of the packing materials. FIG. 18 shows the relationship between the specific surface area (after the modification with the functional group) and the exchange capacity. From FIG. 18, it can be seen that a packing material having the larger specific surface area tends to have the larger exchange capacity.

TABLE 4

|  | Particle size ($\mu$m) | Specific surface area ($m^2/g$) | Exchange capacity (meq/g) |
|---|---|---|---|
| Example 11 | 3.5 ± 0.5 | 20 | 0.30 |
| Example 13 | 3.5 ± 0.5 | 40 | 0.35 |
| Example 14 | 3.5 ± 0.5 | 70 | 0.50 |
| Comparative Example 5 | 3.5 ± 0.5 | 4 | 0.10 |
| Comparative Example 6 | 3.5 ± 0.5 | 180 | 0.80 |

Figure 19:
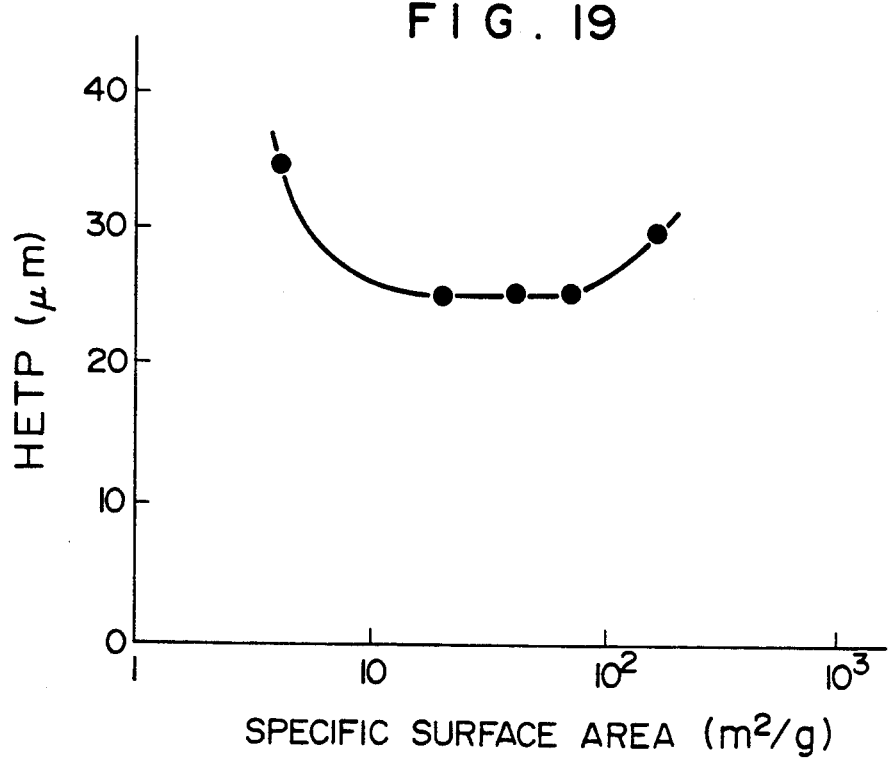
FIG. 19 is a graph showing the relationship between specific surface area and HETP.

Each of the packing materials was packed into a column having an inside diameter of 4.6 mm and a length of 35 mm, and the columns thus treated were used as separation columns. The packing was conducted in the same manner as in Comparative Example 4. HETP of each separation column was measured at various flow rates of eluent as in FIG. 17 (Examples 10 to 12 and Comparative Examples 3 and 4). FIG. 19 shows the relationship between the value of HETP at a flow rate of eluent of 1.0 ml/min and the specific surface area of packing material. In Comparative Example 5 (the packing material having a specific surface area of 4 $m^2/g$), the value of HETP and the peak width were large. It is conjectured that the reason for this is that the packing material had no sufficient area for contact with a sample, so that the sample did not undergo rapid exchange reaction with the sample. Also in Comparative Example 6 (a packing material having a specific surface area of 180 $m^2/g$), an increased HETP value was obtained. In general, a packing material having the smaller pore size tends to have the larger specific surface area. It can be specurated that in Comparative Example 6, the pore size was small, so that a sample could not go in and out of pores, resulting in broadened peaks. In view of the above, the specific surface area of packing material is preferably 10 to 100 $m^2/g$.

EXAMPLES 11, 15 AND 16 AND COMPARATIVE EXAMPLES 7 AND 8

Carboxymethyl groups were combined to the base material consisting of a methacrylate gel of Example 11 under various conditions. Table 5 shows the results of measuring physical properties of the packing materials thus obtained.

TABLE 5

|  | Particle size ($\mu$m) | Specific surface area ($m^2/g$) | Exchange capacity (meq/g) |
|---|---|---|---|
| Example 11 | 3.5 ± 0.5 | 20 | 0.30 |
| Example 15 | 3.5 ± 0.5 | 18 | 0.15 |
| Example 16 | 3.5 ± 0.5 | 20 | 0.55 |
| Comparative Example 7 | 3.5 ± 0.5 | 20 | 2.0 |
| Comparative Example 8 | 3.5 ± 0.5 | 18 | 0.05 |

Figure 20:
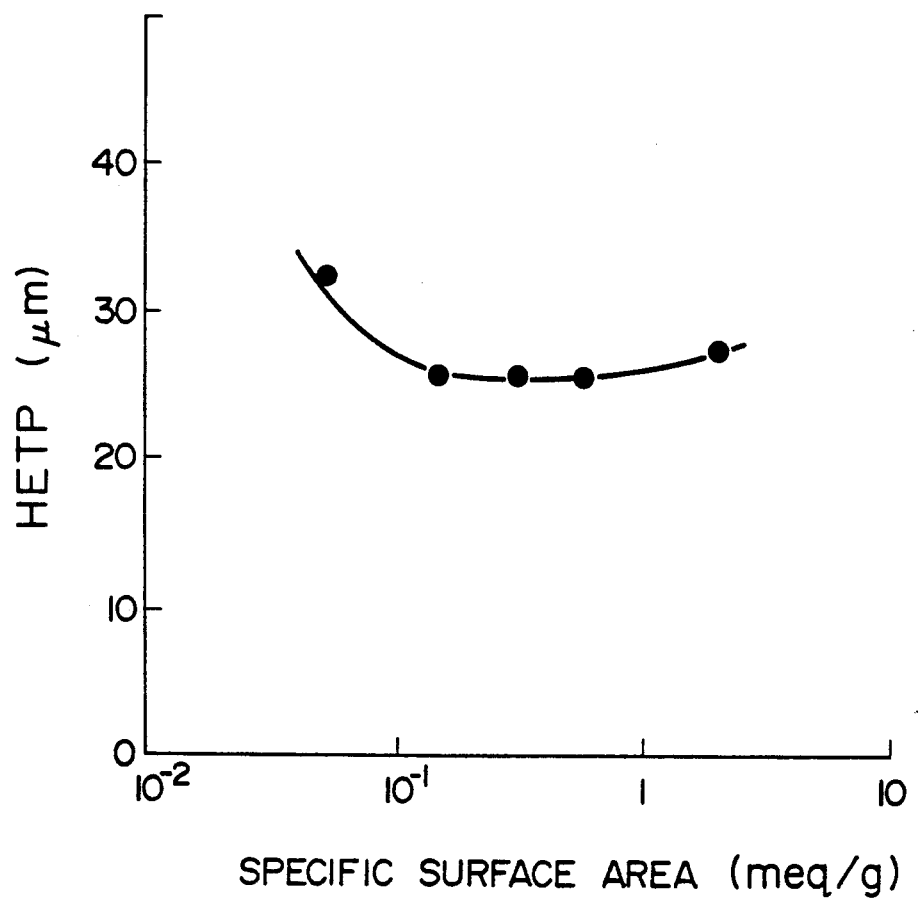
FIG. 20 is a graph showing the relationship between exchange capacity and HETP.

Each of the packing materials was packed into a column having an inside diameter of 4.6 mm and a length of 35 mm, and the columns thus treated were used as separation columns. The packing was conducted in the same manner as in Comparative Example 3. HETP of each separation column was measured at various flow rates of eluent as in FIG. 17 (Examples 10 to 12 and Comparative Examples 3 and 4). FIG. 20 shows the relationship between the value of HETP at a flow rate of eluent of 1.0 ml/min and the exchange capacity of packing material. In Comparative Example 8 (a packing material having an exchange capacity of 0.05 meq/g), an increased HETP value was obtained. It is conjectured that the reason for this is that the amount of the functional group (carboxymethyl group) introduced was too small, so that a sample did not undergo rapid exchange reaction with the packing material. Also in Comparative Example 7 (a packing material having an exchange capacity of 2.0 meq/g), a somewhat increased HETP value was obtained. When the salt concentration of eluent was changed, a packing material having a large exchange capacity is swollen or shrunk more seriously than does a Packing material having a small exchange capacity. Employment of a packing material having a large exchange capacity tends to result in a large pressure drop of column. It is conjectured that the increased HETP value is due to such unstability of the packing material of Comparative Example 7 in a solvent (an eluent) and its low permeability. A packing material having a large exchange capacity is insufficient in life when gradient elution is carried out. In view of these facts, the exchange r capacity of packing material is preferably 0.1–1 meq/g.

As described above, the present invention is effective in that it permits preparation of a separation column having a high chromatographic performance and hence makes it possible to carry out analysis for s-$A_{lc}$ which have heretofore required a long time (8 to 60 minutes), in a short time (3.5 minutes).

The present invention is effective also in that since it permits preparation of a separation column having a high separation efficiency and a rapid rate of exchange with eluent, it makes it possible to carry out analyses such as 5-components analysis (components to be separated: $A_{la}$, $A_{lb}$, HbF, $A_{lc}$ and HbA$_0$), 6-components analysis (components to be separated: $A_{la}$, $A_{lb}$, HbF, l-$A_{lc}$, s-$A_{lc}$ and HbA$_0$, multi-components (more than 6 components) analysis (precise analysis), etc. in succession by the same column and the same eluents only by changing elution conditions, i.e., the program of gradient. According to the present invention, a plurality of analyses can be carried out in succession without exchanging eluents or a separating column, so that time required for the analyses can be reduced, in the present invention, operations are easy (there are not required the trouble of exchanging a separation column or eluents, and the trouble of passing an eluent until a separation column becomes stable).

According to the present invention, there can be provided a method for liquid chromatography and an apparatus or system therefore, which permit high-speed analysis for components of hemoglobin, glycosylated hemoglobin, hemoglobin derivatives, etc. in blood.

There can also be provided a method for liquid chromatography and an apparatus or system therefore, which permit high-precision analysis for components of hemoglobin, glycosylated hemoglobin, hemoglobin derivatives, etc. in blood.

In addition, there can be provided a system for liquid chromatography which makes it possible to carry out various analyses for components in succession automatically.

What is claimed is:

1. An apparatus for liquid chromatography for measuring hemoglobin, hemoglobins derivatives or glycosylated hemoglobin in blood, which comprises:
    a separation column packed with packing material obtained by introducing a carboxyalkyl group into an inorganic porous substance or an organic porous substance;
    a means for injecting a sample into the separation column;
    a means for passing one or more eluents through the separation column for separating labile-$A_{lc}$ and stable $A_{lc}$ from hemoglobin in blood;
    and a means for detecting the absorbances of eluates from the separation column,
    the average particle size of said packing material in dry state being 4 μm or less, and said packing material having a specific surface area in dry state of 10 to 100 m$^2$/g and an exchange capacity per gram on dry basis of 0.1–1 meq.

2. An apparatus for liquid chromatography according to claim 1, wherein the carboxyalkyl group is a carboxymethyl group.

3. An apparatus for liquid chromatography according to claims 1, wherein the eluent(s) are buffer solution(s) having a pH of 5.0 to 7.0.

4. A system for liquid chromatography for determining hemoglobin, hemoglobin derivatives or glycosylated hemoglobin in blood, which comprises:
    one or ore eluents for separating labile-$A_{lc}$ and stable-$A_{lc}$ and for separating $A_{lc}$ components from hemoglobins in blood;
    a separation column;
    a means for detecting components separated in the separation column;
    a calculation means for calculating the proportions of the components;
    a processing means for processing data from the calculation means, to judge whether the proportion of $A_{lc}$ exceeds a predetermined value;
    a means for varying the flow rate, switching times, compositions or mixing rate of the one or more eluents flowing into the separation column, on the basis of signal(s) from the processing means, thereby allowing separation of $A_{lc}$ component from hemoglobins in blood and separation of labile-$A_{lc}$ and stable-$A_{lc}$ from hemoglobins in blood to be continuously effected in said separation column.

5. A system for liquid chromatography according to claim 4, wherein the separation column is packed with a packing material obtained by introducing a functional group into an inorganic or organic porous substance, the average particle size of the packing material in dry state being 4 μm or less, the specific surface area of the packing material in a dry state being 10 to 100 m$^2$/g, and the exchange capacity per gram on a dry basis being 0.1 to 1 meq.

6. A system for liquid chromatography according to claim 5, wherein said functional group is a carboxyalkyl group.

7. A system for liquid chromatography according to claim 6, wherein said carboxyalkyl group is a carboxymethyl group.

8. An apparatus for liquid chromatography for fractionating hemoglobin into a plurality of fractions by flowing stepwise two or more eluents into a separation column, comprising a separation column, means for calculating proportions of components separated by said separation column, processing means for processing data from the calculation means and means for varying the mixing ratio, switching times or flow rate of two or more eluents on the basis of signals from the processing means to enable the determination of the proportion of $A_{lc}$ components and the determination of the proportions of labile-$A_{lc}$ and stable-$A_{lc}$ in the same said separation column by using the same said two or more eluents.

9. An apparatus according to claim 8, wherein said separation column is packed with a packing material obtained by introducing a carboxyalkyl group into an inorganic porous substance or an organic porous substance, the average particle size of the packing material in dry state being 4 μm or less the specific surface area of the packing material in dry state being 10 to 100 m$^2$/g, and the exchange capacity of the packing material per gram on a dry basis being 0.1 to 1 meq.

10. An apparatus according to claim 9, wherein said carboxyalkyl group is a carboxymethyl group.

* * * * *